(12) United States Patent
Yofu

(10) Patent No.: US 9,371,460 B2
(45) Date of Patent: Jun. 21, 2016

(54) PHOTOPOLYMERIZATION METHOD, INK SET, INK COMPOSITION, AND WATER-SOLUBLE BIIMIDAZOLE

(71) Applicant: FUJIFILM CORPORATION, Tokyo (JP)

(72) Inventor: Katsuyuki Yofu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/611,694

(22) Filed: Feb. 2, 2015

(65) Prior Publication Data

US 2015/0148442 A1  May 28, 2015

Related U.S. Application Data

(63) Continuation of application No. PCT/JP2013/073012, filed on Aug. 28, 2013.

(30) Foreign Application Priority Data

Sep. 20, 2012 (JP) .................... 2012-207631
Mar. 22, 2013 (JP) .................... 2013-061109

(51) Int. Cl.
| | |
|---|---|
| C08F 2/46 | (2006.01) |
| B29C 71/04 | (2006.01) |
| C08G 61/04 | (2006.01) |
| C09D 11/30 | (2014.01) |
| C07D 233/88 | (2006.01) |
| C08F 2/50 | (2006.01) |
| B41M 7/00 | (2006.01) |
| C09D 11/101 | (2014.01) |
| C09D 11/40 | (2014.01) |
| C07D 233/58 | (2006.01) |
| C07D 233/64 | (2006.01) |
| C09D 133/08 | (2006.01) |
| C09D 133/26 | (2006.01) |

(52) U.S. Cl.
CPC ............. *C09D 11/30* (2013.01); *B41M 7/0081* (2013.01); *C07D 233/58* (2013.01); *C07D 233/64* (2013.01); *C07D 233/88* (2013.01); *C08F 2/50* (2013.01); *C09D 11/101* (2013.01); *C09D 11/40* (2013.01); *C09D 133/08* (2013.01); *C09D 133/26* (2013.01)

(58) Field of Classification Search
CPC .... C09D 11/30; C09D 133/26; C09D 133/08; C07D 233/58; C07D 233/64; C07D 233/88; C08F 2/50
USPC ............. 522/57, 49, 6, 71, 189, 184, 1; 520/1
See application file for complete search history.

(56) References Cited

U.S. PATENT DOCUMENTS

| | | | |
|---|---|---|---|
| 8,393,725 B2 | 3/2013 | Irita | |
| 2006/0128823 A1* | 6/2006 | Tsuchimura | ......... C09D 11/101 522/71 |
| 2007/0212641 A1* | 9/2007 | Wakata | .................. G03F 7/033 430/270.1 |

FOREIGN PATENT DOCUMENTS

| | | |
|---|---|---|
| CN | 101735400 A | 6/2010 |
| JP | 2000-098124 A | 4/2000 |
| JP | 2003-206307 A | 7/2003 |
| JP | 2007-270079 A | 10/2007 |
| JP | 2011-046871 A | 3/2011 |

OTHER PUBLICATIONS

International Search Report; PCT/JP2013/073012; Dec. 3, 2013.
(Continued)

*Primary Examiner* — Ling Choi
*Assistant Examiner* — Jessica E Whiteley
(74) *Attorney, Agent, or Firm* — Studebaker & Brackett PC

(57) ABSTRACT

A photopolymerization method in which an ink composition including (A) a polymerizing compound having an ethylenic unsaturated group, (B) a photopolymerization initiator represented by Formula (1) described below, and (C) a hydrogen donor having a structure in which a nitrogen atom is directly bonded to an aromatic ring, in which the aromatic ring has an electron-withdrawing group or the nitrogen atom constitutes a hetero ring, is photopolymerized under acidic conditions,

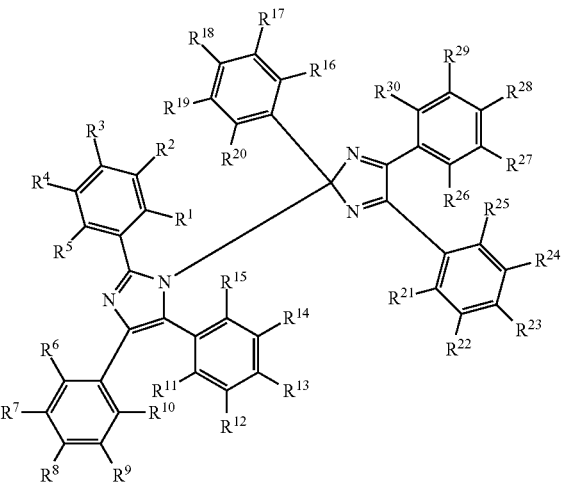

FORMULA (1)

in Formula (1), each of $R^1$ to $R^{30}$ represents a hydrogen atom, a halogen atom, an alkyl group, or an alkoxy group.

8 Claims, No Drawings

(56) References Cited

OTHER PUBLICATIONS

Chem. Abstr., 1967, 66, 50700.
An Office Action issued by the Chinese Patent Office on Oct. 9, 2015, which corresponds to Chinese Patent Application No. 201380042942.X and is related to U.S. Appl. No. 14/611,694; with English language translation.

* cited by examiner

PHOTOPOLYMERIZATION METHOD, INK SET, INK COMPOSITION, AND WATER-SOLUBLE BIIMIDAZOLE

CROSS-REFERENCE TO RELATED APPLICATIONS

This application is a Continuation of PCT International Application No. PCT/JP2013/73012, filed on Aug. 28, 2013, which claims priority under 35 U.S.C. §119(a) to Japanese Patent Application No. 2012-207631, filed on Sep. 20, 2012, and to Japanese Patent Application No. 2013-061109, filed on Mar. 22, 2013. Each of the above application(s) is hereby expressly incorporated by reference, in its entirety, into the present application.

BACKGROUND OF THE INVENTION

1. Field of the Invention

The present invention relates to a photopolymerization method, an ink set, an ink composition, and a water-soluble biimidazole.

2. Description of the Related Art

As an image-recording method in which an image is formed on a recording medium such as paper on the basis of an image data signal, there are an electrophotographic method, a sublimation-type or melting-type thermal transfer method, an ink jet method, and the like.

In the ink jet method, the operation cost is inexpensive because a plate is not required during printing, and an ink composition can be efficiently used by directly forming an image on a recording medium by discharging the ink composition only in necessary image sections. Furthermore, in the ink jet method, an inexpensive printing device is used, and only a small amount of noise is generated. As described above, the ink jet method has a variety of advantages compared with other image-recording methods.

As an ink composition used in the ink jet method, a radiation curable ink composition is known. The radiation curable ink composition is cured by the polymerization of a polymerizing component in the ink composition through radiation of a radioactive ray such as an ultraviolet ray, and thus has an advantage that ink is not easily bled from an image compared with a case in which a radiation non-curable ink composition (a solvent-based ink composition) is used.

In recent years, there has been a demand for use of an LED as a UV light source for curing the radiation curable ink composition from the viewpoint of energy saving and space saving. However, α-hydroxyacetophenone-based photopolymerization initiator, which is a photopolymerization initiator widely used for radiation curing, has a short (approximately 280 nm) absorption wavelength, and thus is almost incapable of polymerizing an ink composition with a UV-LED light source (approximately 365 nm).

Meanwhile, in a system in which a biimidazole-based photopolymerization initiator is used, it has been reported that the sensitivity is improved by combining the biimidazole-based photopolymerization initiator with an amine-based, thiol-based, or disulfide-based hydrogen donor (refer to JP2000-98124A, JP2003-206307A, and Chem. Abstr., 1967, 66, 50700).

SUMMARY OF THE INVENTION

However, even when the biimidazole-based photopolymerization initiator and the specific hydrogen donor described above are combined together, it cannot be said that the photopolymerization initiation performance is sufficient when the UV-LED light source is used.

An object of the present invention is to provide a photopolymerization method for photopolymerizing an ink composition including a polymerizing compound and a photopolymerization initiator in which a photopolymerization reaction can be initiated as efficiently as a case in which the UV-LED light source is used even when a UV ray having a long wavelength is radiated, and therefore the photopolymerization ratio of a polymerizing component can be further improved.

In addition, an object of the present invention is to provide an ink set preferable for use in the above-described photopolymerization method and an ink composition preferable for the above-described ink set.

In addition, an object of the present invention is to provide a biimidazole compound preferable as a photopolymerization initiator used in the photopolymerization method.

In addition, an object of the present invention is to provide an image-forming method in which bleeding and the like are further suppressed.

As a result of intensive studies in consideration of the above-described objects, the present inventors found that, when a polymerizing compound having an ethylenic unsaturated group is photopolymerized using a UV-LED light source (having a light-emitting wavelength of approximately 365 nm), the coexistence of a specific photopolymerization initiator and a specific hydrogen donor produces excellent photopolymerization efficiency, particularly under acidic conditions. In addition, it was found that the use of a composition including the respective components described above and a colorant as ink in photopolymerizatin enables the formation of a more robust and highly accurate image from which the ink is not easily bled. The present invention has been completed by repeating additional studies on the basis of the above-described findings.

The objects of the present invention have been achieved by the following means.

<1> A photopolymerization method in which an ink composition including (A) a polymerizing compound having an ethylenic unsaturated group, (B) a photopolymerization initiator represented by Formula (1) described below, and (C) a hydrogen donor having a structure in which a nitrogen atom is directly bonded to an aromatic ring, in which the aromatic ring has an electron-withdrawing group or the nitrogen atom constitutes a hetero ring, is photopolymerized under acidic conditions.

[Chem. 1]

FORMULA (1)

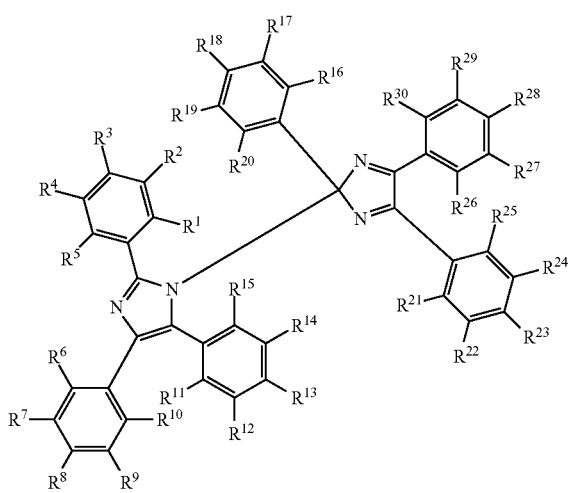

In Formula (1), each of $R^1$ to $R^{30}$ represents a hydrogen atom, a halogen atom, an alkyl group, or an alkoxy group.

<2> The photopolymerization method according to <1> in which the ink composition includes (D) trialkylamine.

<3> The photopolymerization method according to <1> or <2> in which (C) the hydrogen donor is represented by Formula (2) or (3) described below.

[Chem. 2]

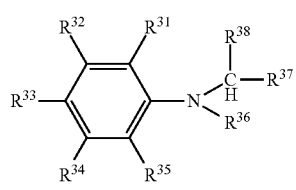

FORMULA (2)

[Chem. 3]

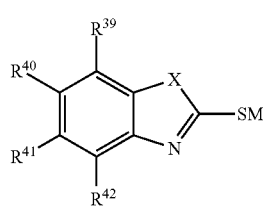

FORMULA (3)

In Formulae (2) and (3), each of $R^{31}$ to $R^{35}$ and $R^{39}$ to $R^{42}$ represents a hydrogen atom or a substituent. Here, at least one of $R^{31}$ to $R^{35}$ is an electron-withdrawing group. $R^{36}$ represents a hydrogen atom, an alkyl group, or an aryl group. Each of $R^{37}$ and $R^{38}$ represents a hydrogen atom or an alkyl group. X represents an oxygen atom, a sulfur atom, or a nitrogen atom having a substituent. M represents a hydrogen atom or an alkali metal.

<4> The photopolymerization method according to <3> in which each of $R^{31}$ to $R^{35}$ in Formula (2) is a group selected from a hydrogen atom, an alkyl group, an alkoxy group, and an electron-withdrawing group, at least one of $R^{31}$ to $R^{35}$ is an electron-withdrawing group, and the electron-withdrawing group is a group selected from halogen atoms, a fluoroalkyl group, a cyano group, an acyl group, an alkoxycarbonyl group, an aryloxy carbonyl group, a carbamoyl group, an alkylsulfonyl group, an arylsulfonyl group, an alkylsulfamoyl group, and an arylsulfamoyl group.

<5> The photopolymerization method according to <3> in which each of $R^{39}$ to $R^{42}$ in Formula (3) is a group selected from a hydrogen atom, an alkyl group, an alkoxy group, halogen atoms, a fluoroalkyl group, a cyano group, an acyl group, an amino group, an ammonio group, an alkoxycarbonyl group, an aryloxy carbonyl group, a carbamoyl group, an alkylsulfonyl group, an arylsulfonyl group, an alkylsulfamoyl group, and an arylsulfamoyl group.

<6> The photopolymerization method according to any one of <1> to <5> in which (A) the polymerizing compound having an ethylenic unsaturated group is a (meth)acrylate compound having two or more (meth)acryloyl groups or a (meth)acrylamide compound having two or more (meth)acrylamide groups.

<7> The photopolymerization method according to any one of <1> to <6> in which the ink composition is an ink composition including (E) a colorant.

<8> The photopolymerization method according to <7> in which the ink composition is an ink composition for an ink jet.

<9> The photopolymerization method according to <7> or <8> in which an image is formed using the ink composition, and the polymerizing compound in the image is photopolymerized by radiating light on the image.

<10> An ink set including an ink composition including (A) a polymerizing compound having an ethylenic unsaturated group, (B) a photopolymerization initiator represented by Formula (1) described below, and (C) a hydrogen donor having a structure in which a nitrogen atom is directly bonded to an aromatic ring, in which the aromatic ring has an electron-withdrawing group or the nitrogen atom constitutes a hetero ring, and an acid treatment agent including an acidic compound.

[Chem. 4]

FORMULA (1)

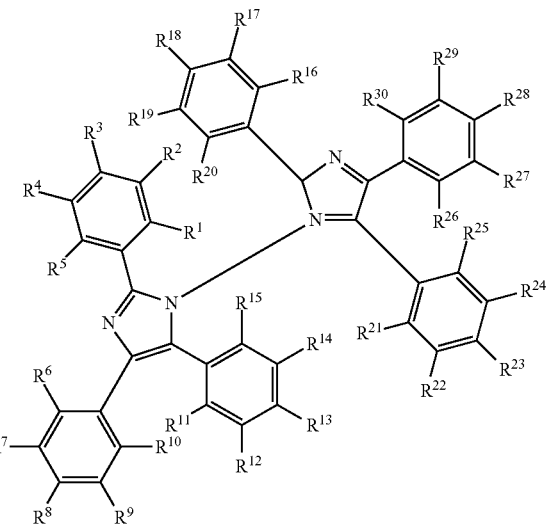

In Formula (1), each of $R^1$ to $R^{30}$ represents a hydrogen atom, a halogen atom, an alkyl group, or an alkoxy group.

<11> The ink set according to <10> in which the ink composition includes (D) trialkylamine.

<12> The ink set according to <10> or <11> in which (C) the hydrogen donor is represented by Formula (2) or (3) described below.

[Chem. 5]

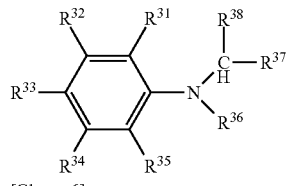

FORMULA (2)

[Chem. 6]

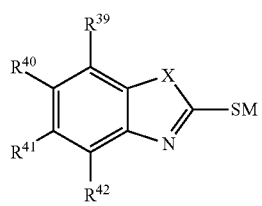

FORMULA (3)

In Formulae (2) and (3), each of $R^{31}$ to $R^{35}$ and $R^{39}$ to $R^{42}$ represents a hydrogen atom or a substituent. Here, at least one of $R^{31}$ to $R^{35}$ is an electron-withdrawing group. $R^{36}$ represents a hydrogen atom, an alkyl group, or an aryl group. Each of $R^{37}$ and $R^{38}$ represents a hydrogen atom or an alkyl group. X represents an oxygen atom, a sulfur atom, or a nitrogen atom having a substituent. M represents a hydrogen atom or an alkali metal.

<13> The ink set according to any one of <10> to <12> in which the acidic compound is an acid having a molecular weight in a range of 50 to 200 and a pKa in water in a range of 1 to 5.

<14> The ink set according to any one of <10> to <13> in which (A) the polymerizing compound having an ethylenic unsaturated group is a (meth)acrylate compound having two or more (meth)acryloyl groups or a (meth)acrylamide compound having two or more (meth)acrylamide groups.

<15> The ink set according to any one of <10> to <14> in which the ink composition includes (E) a colorant.

<16> The ink set according to any one of <10> to <15> in which the ink set is an ink set for an ink jet.

<17> An image-forming method in which the photopolymerization method according to any one of <1> to <9> is used.

<18> An image-forming method in which the ink set according to any one of <10> to <16> is used.

<19> The image-forming method according to <18> including an acid treatment step of supplying an acid treatment agent onto a recording medium, an ink-supplying step of supplying an ink composition onto the recording medium after the acid treatment step, thereby forming an image, and a photopolymerization step of polymerizing the polymerizing compounds in the image through light radiation.

<20> An ink composition including (A) a polymerizing compound having an ethylenic unsaturated group, (B) a photopolymerization initiator represented by Formula (1) described below, and (C) a hydrogen donor represented by Formula (2') described below.

[Chem. 7]

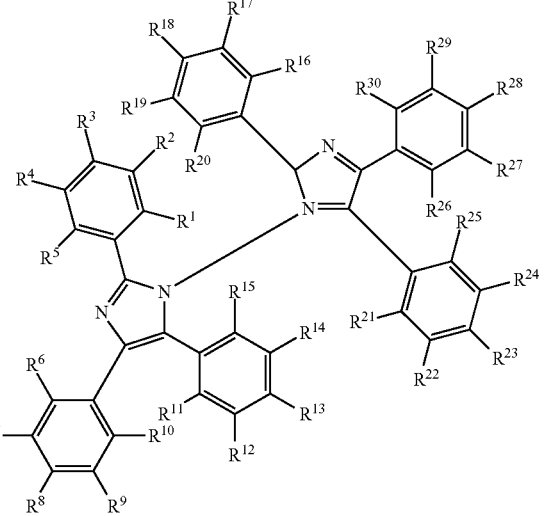

FORMULA (1)

In Formula (1), each of $R^1$ to $R^{30}$ represents a hydrogen atom, a halogen atom, an alkyl group, or an alkoxy group.

[Chem. 8]

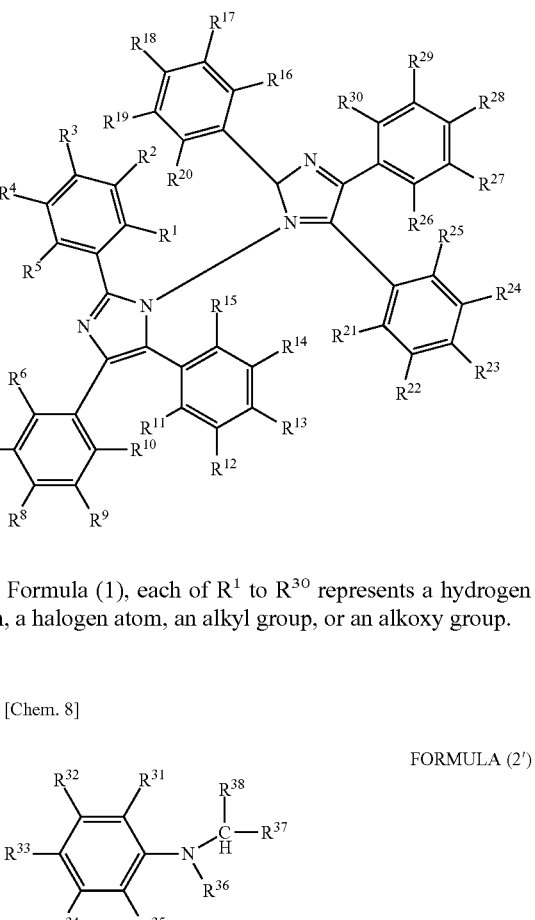

FORMULA (2')

In Formula (2'), each of $R^{31}$ to $R^{35}$ represents a hydrogen atom or a substituent. Here, at least one of $R^{31}$ to $R^{35}$ is an electron-withdrawing group having a positive Hammett σ value. $R^{36}$ represents a hydrogen atom, an alkyl group, or an aryl group. Each of $R^{37}$ and $R^{38}$ represents a hydrogen atom or an alkyl group.

<21> The ink composition according to <20> including (D) trialkylamine.

<22> The ink composition according to <20> or <21> including (E) a colorant.

<23> A water-soluble biimidazole represented by Formula (1') described below.

[Chem. 9]

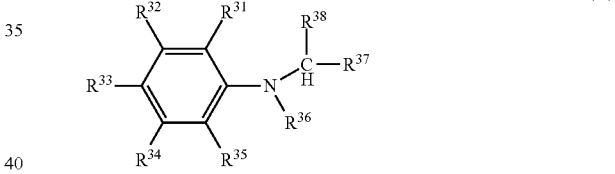

-continued

FORMULA (1')

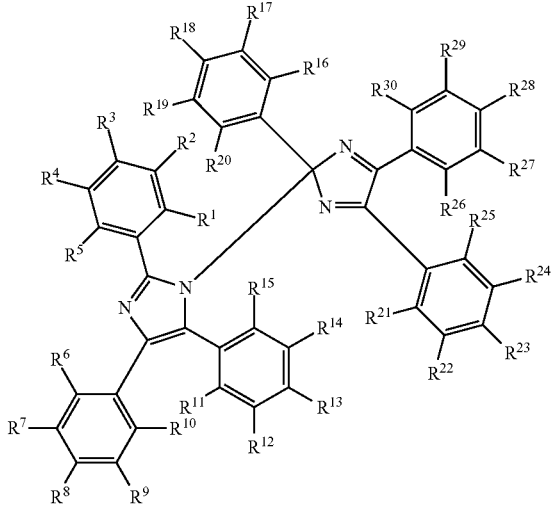

In Formula (1'), each of $R^1$ to $R^{30}$ represents a hydrogen atom, a halogen atom, an alkyl group, or an alkoxy group. Here, at least one of $R^1$ to $R^{30}$ is an alkyl group or an alkoxy group having an ionic group or a salt thereof.

<24> The water-soluble biimidazole according to <23> in which the ionic group represents a carboxyl group, a sulfo group, or —$N^+(R^a)_2$-$L^a$-$R^b$, $R^a$ represents a hydrogen atom or an alkyl group having 1 to 10 carbon atoms, $L^a$ represents a single bond or an alkylene group having 1 to 10 carbon atoms, and $R^b$ represents an alkyl group having 1 to 5 carbon atoms, a carboxyl group, or a sulfo group.

<25> A photopolymerization initiator constituted of the water-soluble biimidazole according to <23> or <24>.

In the present specification, "(meth)acryloyl" refers to either or both acryloyl (—C(=O)CH=CH$_2$) and methacryloyl (—C(=O)C(CH$_3$)=CH$_2$). This also shall apply to terminologies of "(meth)acryl", "(meth)acrylate", and "(meth)acrylamide".

In the present specification, unless particularly described otherwise, when there are a plurality of substituents, coupling groups, ligands, and the like (hereinafter, referred to as substituents and the like) indicated by specific reference signs, or a plurality of substituents and the like are simultaneously or selectively regulated, the respective substituents and the like may be identical to or different from each other. This also shall apply when the numbers of substituents and the like are regulated. In addition, in a case in which there are a plurality of partial structures or repeating units indicated by the same mark in formulae, the respective partial structures or repeating units may be identical to or different from each other.

In the present specification, "groups" of individual groups described as examples of the respective substituents refer to unsubstituted groups and groups having a substituent. For example, an "alkyl group" refers to an alkyl group which may have a substituent.

In the present specification, when a substance is called its name with "compound" at the end or a compound is indicated by a specific name or a chemical formula, unless particularly described otherwise, the compound refers not only to the compound itself but also to salts, complexes, and ions thereof.

In the present specification, "the total amount of a solid content" refers to the total mass of all components in a composition excluding a solvent component, that is, the total mass of non-volatile components.

According to the photopolymerization method of the present invention, it is possible to realize an excellent polymerization ratio of a polymerizing component even in a case in which a UV-LED light source (having a light-emitting wavelength of approximately 365 nm) is used.

When the ink set of the present invention is used, it is possible to more efficiently polymerize polymerizing components in an ink composition constituting the ink set even in a case in which a UV-LED light source (having a light-emitting wavelength of approximately 365 nm) is used.

According to the image-forming method of the present invention, it is possible to record a robust and highly accurate image.

The ink composition of the present invention produces superior polymerization efficiency in a case in which the ink composition is irradiated with a UV ray using a UV-LED light source (having a light-emitting wavelength of approximately 365 nm) under acidic conditions.

The water-soluble biimidazole compound of the present invention functions as a photopolymerization initiator with respect to UV radiation from a UV-LED light source (having a light-emitting wavelength of approximately 365 nm) under acidic conditions in the presence of a specific hydrogen donor.

DESCRIPTION OF THE PREFERRED EMBODIMENTS

Hereinafter, the present invention will be described in more detail.

[Ink Composition]

An ink composition used in the present invention (hereinafter, also referred to simply as "ink") includes at least (A) a polymerizing compound having an ethylenic unsaturated group, (B) a biimidazole photopolymerization initiator represented by Formula (1) described below, and (C) a hydrogen donor having a structure in which a nitrogen atom is directly bonded to an aromatic ring, in which the aromatic ring has an electron-withdrawing group or the nitrogen atom constitutes a hetero ring.

That is, the ink composition used in the present invention is a polymerizing composition including one or more types of (A) the components, one or more types of (B) the components, and one or more types of (C) the components.

In addition, the ink composition used in the present invention may include one or more types of (D) trialkylamine. When including trialkylamine, the ink composition is capable of further improving the photopolymerization ratio.

In addition, the ink composition used in the present invention may include one or more types of (E) colorants. When including no colorant, the ink composition can be used as a clear ink, and when including a colorant, the ink composition can be used to form a color image.

The ink composition used in the present invention can be preferably used as ink for forming an image using an ink jet.

When the ink composition used in the present invention includes a combination of the above-described respective components, the ink composition is excellent in terms of polymerization sensitivity under acidic conditions. When an image is formed on a recording medium using the ink composition, and then an active energy ray such as UV or the like is radiated, it is possible to form an image having excellent blocking resistance.

<(A) Polymerizing Compound Having an Ethylenic Unsaturated Group>

The polymerizing compound having an ethylenic unsaturated group (hereinafter, also referred to simply as "polymerizing compound") is a compound including at least one ethylenic unsaturated bond that can be radical-polymerized in the molecule, and is not particularly limited as long as a polymerization reaction of the polymerizing compound can be initiated using a photopolymerization initiator. The polymerizing compound may be any of a monomer, an oligomer, a polymer, and the like.

In the present invention, the molecular weight of the polymerizing compound is preferably in a range of 50 to 2000, more preferably in a range of 80 to 1500, and still more preferably in a range of 100 to 800 from the viewpoint of satisfying both film quality improvement and solubility.

Meanwhile, the ethylenic unsaturated group is a group having a carbon to carbon double bond. This carbon to carbon double bond may be conjugated with other saturated bonds, but a double bond in a stable aromatic ring such as a benzene ring is not included in the scope of the ethylenic unsaturated group.

Examples of the ethylenic unsaturated group include a vinyl group (—CH=CH$_2$), a (meth)acryloyl group [—C(=O)CH=CH$_2$ and —C(=O)C(CH$_3$)=CH$_2$], a vinyl sulfonyl group (—SO$_2$CH=CH$_2$), and groups having a partial structure of —C(=O)CH=CHC(=O)— such as maleimide.

Here, examples of a structure having the vinyl group include —O—CH=CH$_2$, >N—CH=CH$_2$, —S—CH=CH$_2$, —O—CH$_2$CH=CH$_2$, —CH=CH$_2$ of styrene, and the like, and examples of a structure having the (meth)acryloyl group include a (meth)acryloyl group, a (meth)acryloyloxy group, a (meth)acryloylamide group, and the like.

The polymerizing compound used in the present invention is preferably a compound having the carbon to carbon double bond at a terminal in the molecule or a compound having a maleimide cyclic group in the molecule.

The polymerizing compound used in the present invention is preferably a water-soluble compound from the viewpoint of the discharging stability of the ink composition. The degree of solubility of the polymerizing compound used in the present invention is not particularly limited, but the degree of solubility in water at 25° C. is preferably 2 mass % or more, more preferably 5 mass % or more, still more preferably 10 mass % or more, particularly preferably 20 mass % or more, and most preferably a degree of solubility at which the polymerizing compound and water are homogeneously mixed with each other at an arbitrary ratio.

Specific examples of the polymerizing compound used in the present invention include (meth)acrylamide compounds, (meth)acrylate compounds, vinyl compounds, maleimide compounds, vinyl sulfone compounds, N-vinylamide compounds, and the like. As the polymerizing compound used in the present invention, a compound having one ethylenic unsaturated group in the molecule may be used; however, from the viewpoint of further improving curing properties, the polymerizing compound used in the present invention preferably has two or more ethylenic unsaturated groups in the molecule, and more preferably has three or more ethylenic unsaturated groups in the molecule. In a case in which a compound having two or more ethylenic unsaturated groups in the molecule is included, a photopolymerization method of the present invention becomes a so-called photo-curing method. The polymerizing compound used in the present invention is preferably a (meth)acrylamide compound, a (meth)acrylate compound, or a vinyl compound, and more preferably a (meth)acrylate compound having two or more (meth)acryloyl groups or a (meth)acrylamide compound having two or more (meth)acrylamide groups. Particularly, a (meth)acrylamide compound having two or more (meth)acrylamide groups in the molecule can be preferably used.

In an ink composition used in the present invention, the polymerizing compound may be singly used, or two or more types of polymerizing compounds may be jointly used. In a case in which two or more types of polymerizing compounds are jointly used, it is preferable to use a mixture of two or more selected from (meth)acrylamide compounds, (meth)acrylate compounds, vinyl compounds, maleimde compounds, vinylsulfo compounds, and N-vinylamide compounds, and it is more preferable that at least one of the above-described compounds be a (meth)acrylamide compound.

In addition, from the viewpoint of improving water-solubility, the polymerizing compound may have a poly(ethyleneoxy) chain, a poly(propyleneoxy) chain, an ionic group (for example, a carboxyl group, a sulfo group, or the like), a hydroxyl group, or the like in the molecule.

—(Meth)Acrylamide Compound—

Hereinafter, specific examples of a monofunctional (meth)acrylamide compound and a polyfunctional (meth)acrylamide compound that can be used in the present invention will be described, but the present invention is not limited thereto.

[Chem. 10]

(MONOFUNCTIONAL (METH)ACRYLAMIDE

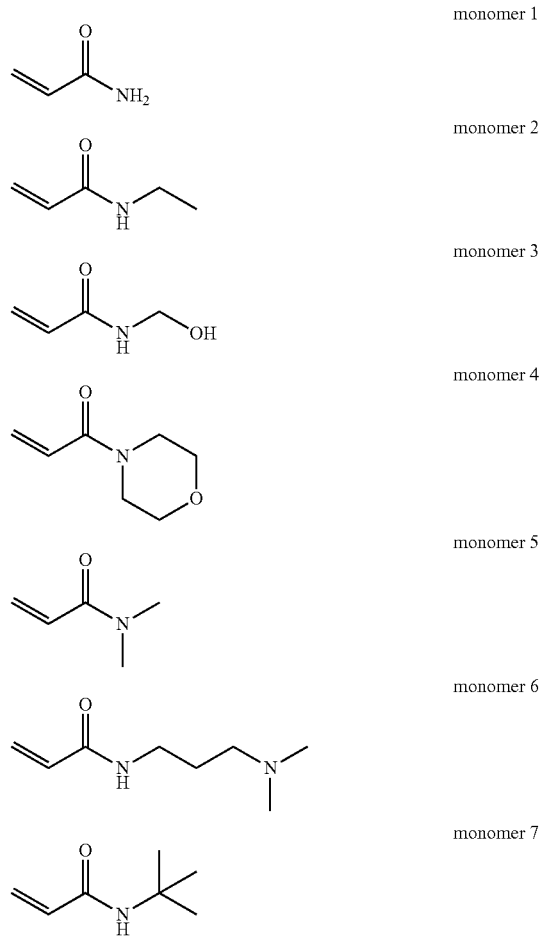

-continued
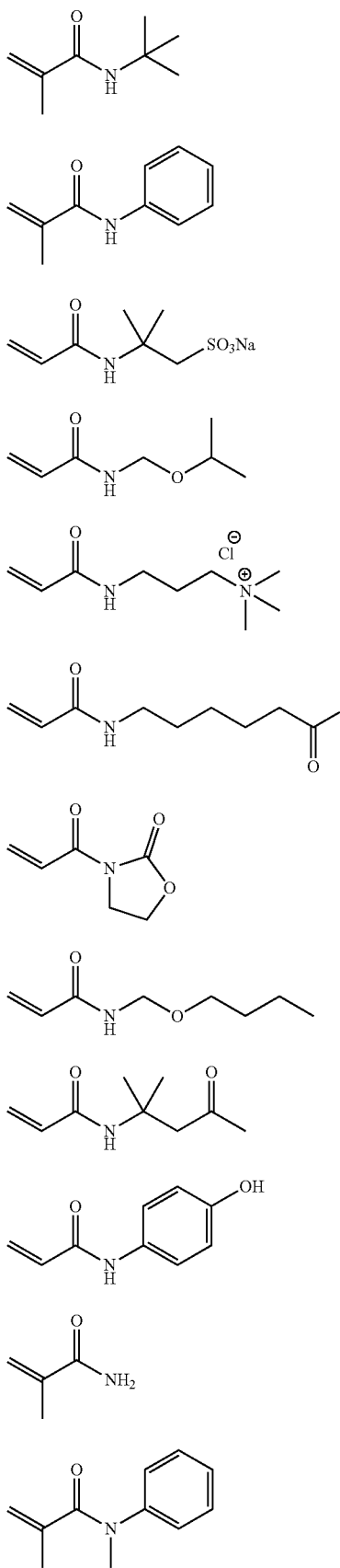
monomer 8
monomer 9
monomer 10
monomer 11
monomer 12
monomer 13
monomer 14
monomer 15
monomer 16
monomer 17
monomer 18
monomer 19
-continued
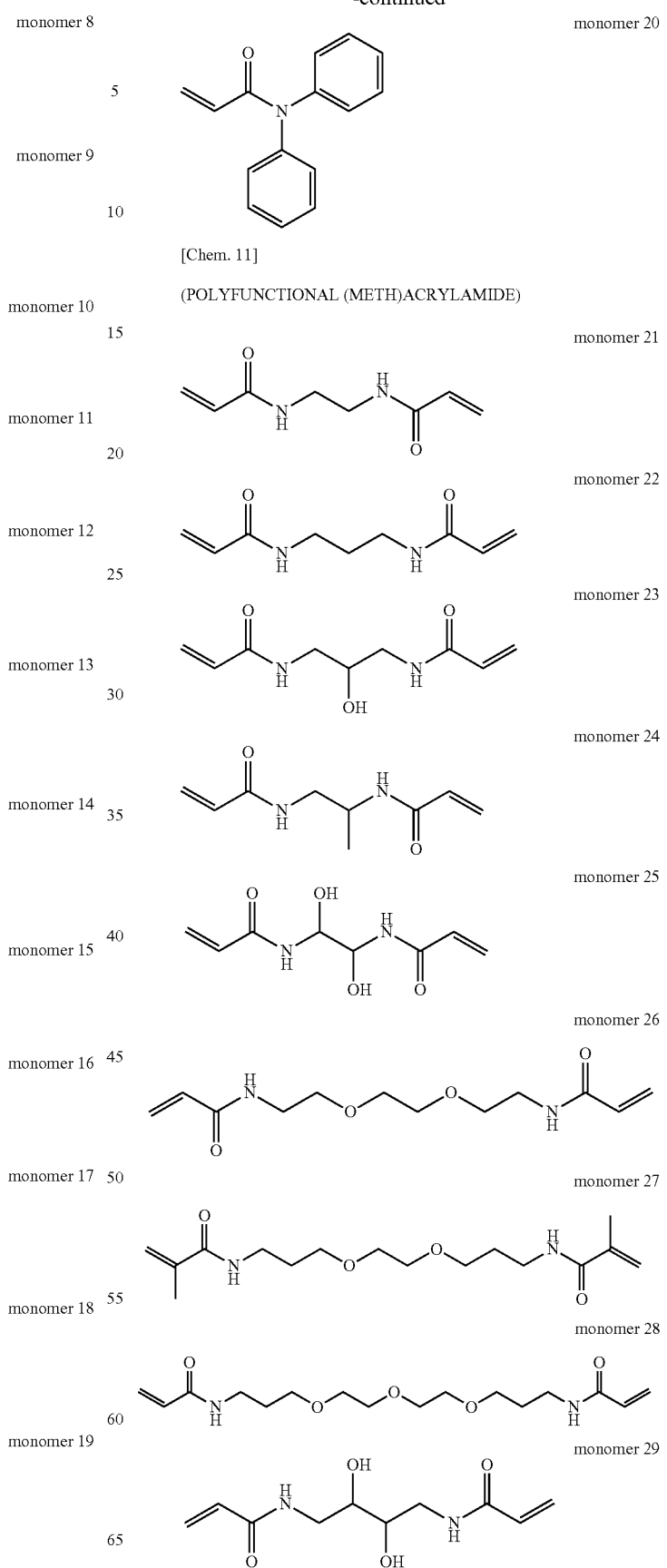
monomer 20
[Chem. 11]
(POLYFUNCTIONAL (METH)ACRYLAMIDE)
monomer 21
monomer 22
monomer 23
monomer 24
monomer 25
monomer 26
monomer 27
monomer 28
monomer 29

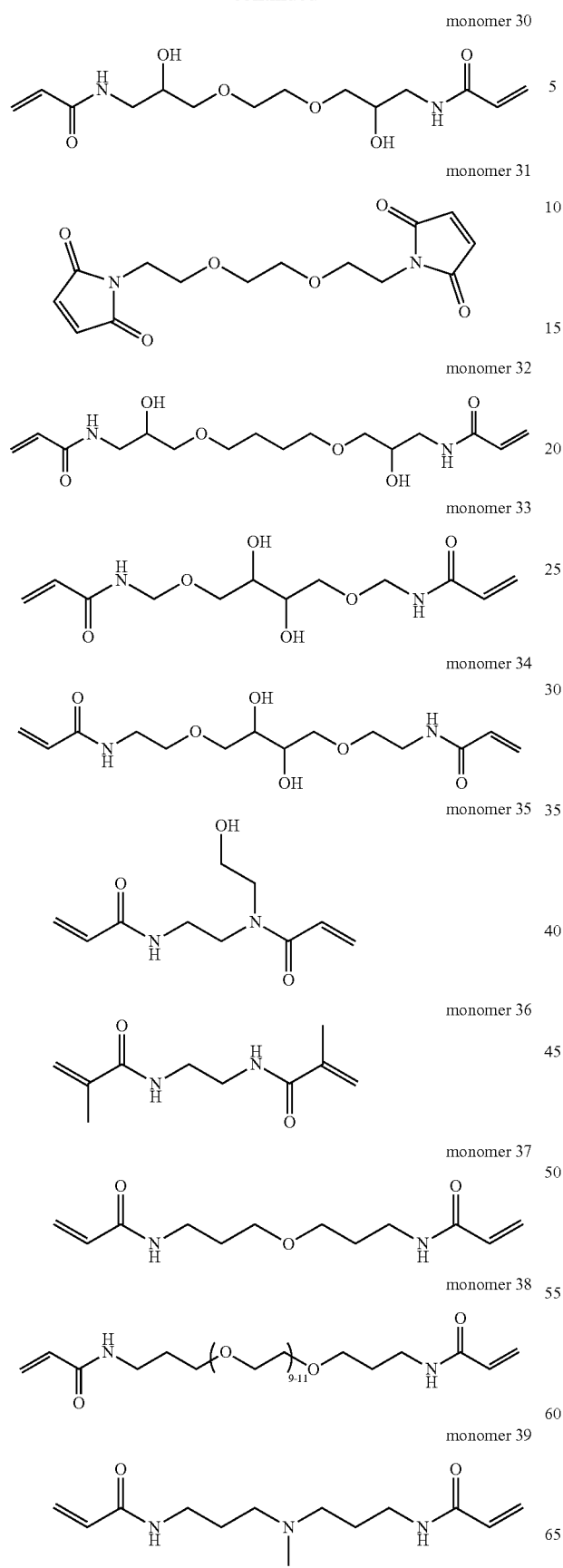
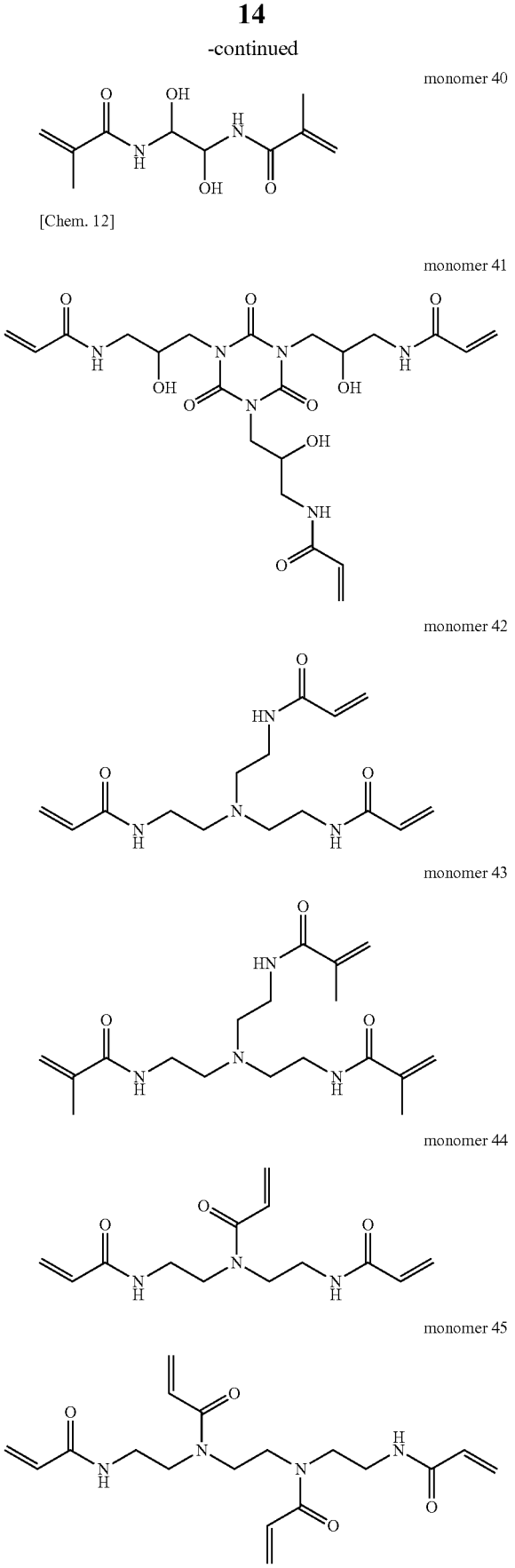

monomer 46
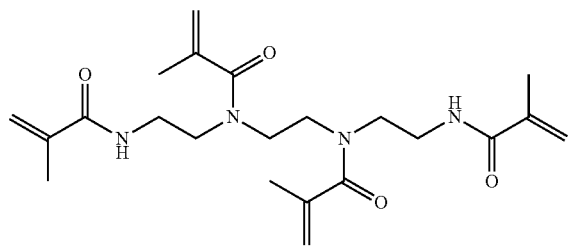

monomer 47
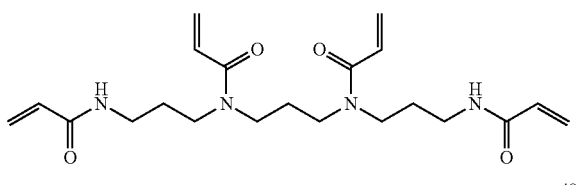

monomer 48
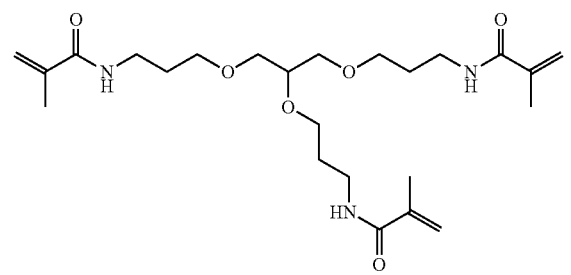

monomer 49
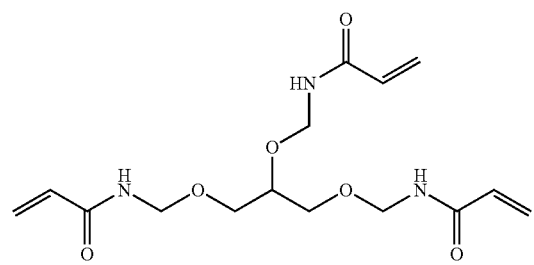

monomer 50
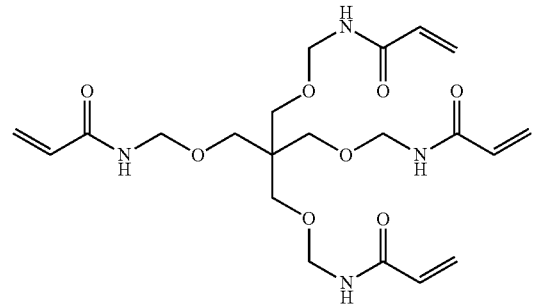

monomer 51
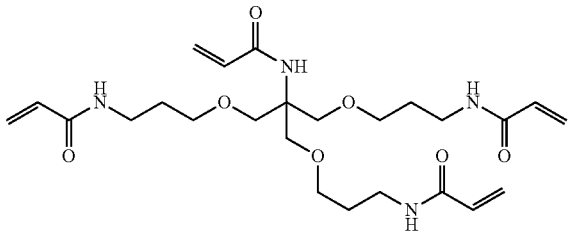

From the viewpoint of curing properties and solubility, among the exemplified acrylamide compounds described above, monomers 21, 27, 28, 42, 44, and 51 are preferably used.

These (meth)acrylamide compounds can be synthesized using an ordinary method for synthesizing an acrylamide compound (for example, Journal of the American Chemical Society, 1979, 101, 5383).

—(Meth)Acrylate Compound—

Hereinafter, specific examples of the monofunctional (meth)acrylate compound and polyfunctional (meth)acrylate compound that can be used in the present invention will be described, but the present invention is not limited thereto.

Specific examples of the monofunctional (meth)acrylate compound include isoamyl (meth)acrylate, stearyl (meth)acrylate, lauryl (meth)acrylate, octyl (meth)acrylate, isooctyl (meth)acrylate, decyl (meth)acrylate, isoamylstyl (meth)acrylate, isostearyl (meth)acrylate, 2-ethylhexyldiglycol (meth)acrylate, 2-hydroxybutyl (meth)acrylate, butoxyethyl (meth)acrylate, methoxydiethyleneglycol (meth)acrylate, methoxypolyethyleneglycol (meth)acrylate, methoxypropyleneglycol (meth)acrylate, tetrahydrofurfuryl (meth)acrylate, isobornyl (meth)acrylate, 2-hydroxyethyl (meth)acrylate, 2-hydroxypropyl (meth)acrylate, 2-(meth)acryloxyethylsuccinic acid, 2-(meth)acryloxyethyl-2-hydroxyethylphthalic acid, lactone denatured flexible (meth)acrylate, t-butylcyclohexyl (meth)acrylate, 2-(2-ethoxyethoxyl)ethyl acrylate, cyclopentenyl acrylate, cyclopentenyloxyethyl acrylate, dicyclopentanyl acrylate, and the like.

Specific examples of the polyfunctional (meth)acrylate compound include bis(4-acryloxypolyethoxyphenyl)propane, neopentyl glycol di(meth)acrylate, ethoxylated (2) neopentyl glycol di(meth)acrylate (a compound obtained by diacrylating neopentyl glycol ethylene oxide 2 mol adduct), propoxylated (2) neopentyl glycol di(meth)acrylate (a compound obtained by diacrylating neopentyl glycol propylene oxide 2 mol adduct), 1,6-hexanediol di(meth)acrylate, 1,9-nonanediol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, dipropylene glycol di(meth)acrylate, tripropylene glycol di(meth)acrylate, tetrapropylene glycol di(meth)acrylate, polypropylene glycol di(meth)acrylate, pentaerythritol tri(meth)acrylate, pentaerythritol tetra(meth)acrylate, dipentaerythritol tetra(meth)acrylate, trimethylolpropane tri(meth)acrylate, tetramethylolmethane tetra(meth)acrylate, tetramethylolmethane tri(meth)acrylate, dimethyloltricyclodecane di(meth)acrylate, denatured glycerine tri(meth)acrylate, denatured bisphenol A di(meth)acrylate, propylene oxide (PO) adduct di(meth)acrylate of bisphenol A, ethylene oxide (EO) adduct di(meth)acrylate of bisphenol A, dipentaerythritol hexa(meth)acrylate, caprolactone-denatured dipentaerythritol hexa(meth)acrylate, and the like.

The content of the polymerizing compound in the ink composition used in the present invention is preferably in a range of 1 mass % to 50 mass %, more preferably in a range of 1 mass % to 40 mass %, and still more preferably in a range of 1 mass % to 30 mass % with respect to a total amount of 100 mass % of the solid content of the ink composition.

<(B) Photopolymerization Initiator>

In the present invention, as the photopolymerization initiator, a biimidazole photopolymerization initiator represented by Formula (1) described below (hereinafter, also referred to simply as "polymerization initiator") is used.

[Chem. 13]

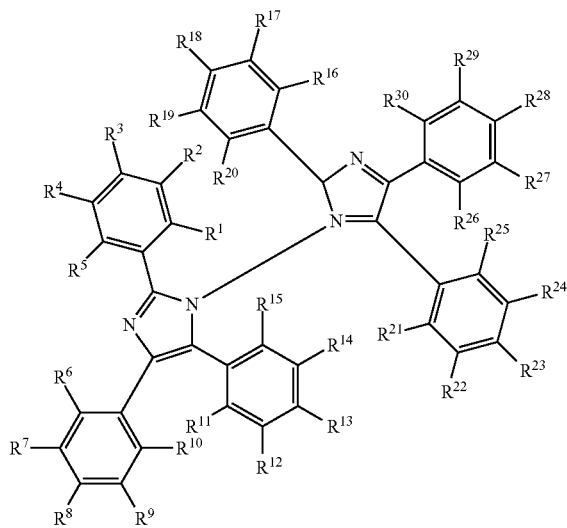

FORMULA (1)

In Formula (1), each of $R^1$ to $R^{30}$ represents a hydrogen atom, a halogen atom, an alkyl group, or an alkoxy group.

Examples of the halogen atom in $R^1$ to $R^{30}$ include a fluorine atom, a chlorine atom, and a bromine atom.

The number of carbon atoms in the alkyl group in $R^1$ to $R^{30}$ is preferably in a range of 1 to 10, more preferably in a range of 1 to 5, and still more preferably in a range of 1 to 3. Examples of the alkyl group include methyl, ethyl, isopropyl, n-propyl, n-butyl, t-butyl, and t-octyl.

The number of carbon atoms in the alkoxy group in $R^1$ to $R^{30}$ is preferably in a range of 1 to 10, more preferably in a range of 1 to 5, and still more preferably in a range of 1 to 3. Examples of the alkoxy group include methoxy, ethoxy, isopropoxy, n-propyloxy, n-butyloxy, and n-octyloxy.

These alkyl groups and alkoxy groups may have a substituent, and examples of the substituent include a hydroxyl group, a carboxyl group, and a sulfo group; —$N^+(R^a)_2$-$L^a$-$R^b$ (here, $R^a$ represents a hydrogen atom or an alkyl group having 1 to 10 carbon atoms (preferably 1 to 5 carbon atoms, and more preferably 1 to 3 carbon atoms), $L^a$ represents a single bond or an alkylene group having 1 to 10 carbon atoms (preferably 1 to 5 carbon atoms, and more preferably 1 to 3 carbon atoms), and $R^b$ represents an alkyl group having 1 to 5 carbon atoms (preferably 1 to 3 carbon atoms), a carboxyl group or a sulfo group (both the carboxyl group and the sulfo group include salts and ions thereof)); an alkyl group (preferably having 1 to 10 carbon atoms, more preferably having 1 to 5 carbon atoms, and still more preferably having 1 to 3 carbon atoms), an aryl group (preferably having 6 to 15 carbon atoms, more preferably having 6 to 13 carbon atoms, and still more preferably having 6 to 10 carbon atoms), a hetero cyclic group (the number of ring members is preferably 5 or 6, the hetero ring may be an aromatic ring or a saturated or unsaturated ring, and a hetero atom of a ring-constituting atom is preferably an oxygen atom, a sulfur atom, and a nitrogen atom), an alkoxy group (preferably having 1 to 10 carbon atoms, more preferably having 1 to 5 carbon atoms, and still more preferably having 1 to 3 carbon atoms), an alkylthio group (preferably having 1 to 10 carbon atoms, more preferably having 1 to 5 carbon atoms, and still more preferably having 1 to 3 carbon atoms), an amino group (including an amino group, an alkylamino group, and an arylamino group), an acyl group (preferably having 2 to 12 carbon atoms, more preferably having 2 to 6 carbon atoms, and still more preferably having 2 to 4 carbon atoms), an alkoxycarbonyl group (preferably having 2 to 12 carbon atoms, more preferably having 2 to 6 carbon atoms, and still more preferably having 2 to 4 carbon atoms), an aryloxy carbonyl group (preferably having 7 to 18 carbon atoms, more preferably having 7 to 14 carbon atoms, and still more preferably having 7 to 12 carbon atoms), an acylamide group (preferably having 2 to 12 carbon atoms, more preferably having 2 to 6 carbon atoms, and still more preferably having 2 to 4 carbon atoms), a sulfonamide group, a carbamoyl group, a sulfamoyl group, an alkylsulfonyl group (preferably having 1 to 10 carbon atoms, more preferably having 1 to 5 carbon atoms, and still more preferably having 1 to 3 carbon atoms), an arylsulfonyl group (preferably having 6 to 15 carbon atoms, more preferably having 6 to 13 carbon atoms, and still more preferably having 6 to 10 carbon atoms), a cyano group, and the like.

The substituent in the alkyl group or the alkoxy group is preferably a hydroxyl group, a carboxyl group, a sulfo group, —$N^+(R^a)_2$-$L^a$-$R^b$ (here, $R^a$, $L^a$, and $R^b$ are identical to $R^a$, $L^a$, and $R^b$ described above), and an alkoxy group. Here, the scope of the alkoxy group also includes an alkoxy group from which an alkyl section is divided by an oxygen atom and which has 2 to 10 repeating units of oxyalkylene.

In addition, in Formula (1), at least one of $R^1$ to $R^{30}$ may be an alkyl group or an alkoxy group having an ionic group or a salt thereof. When the biimidazole photopolymerization initiator has an ionic group, the water solubility is improved, and the solubility of ink for an ink jet in a water-soluble solvent is improved. In addition, the polymerization initiation performance per molecule can also be improved.

The ionic group is represented by a carboxyl group, a sulfo group, or —$N^+(R^a)_2$-$L^a$-$R^b$ (here, $R^a$, $L^a$, and $R^b$ are identical to $R^a$, $L^a$, and $R^b$ described above), and it is preferable that $R^a$ represent a hydrogen atom or an alkyl group having 1 to 10 carbon atoms, $L^a$ represent a single bond or an alkylene group having 1 to 10 carbon atoms, and $R^b$ represent an alkyl group having 1 to 5 carbon atoms, a carboxyl group or a sulfo group.

In Formula (1), each of $R^1$ and $R^{16}$ is preferably a halogen atom, and more preferably a chlorine atom or a bromine atom. In addition, each of $R^8$, $R^{13}$, $R^{23}$, and $R^{28}$ is preferably a hydrogen atom, an alkyl group, or an alkoxy group, and more preferably a hydrogen atom or an alkoxy group (preferably having 1 to 10 carbon atoms, more preferably having 1 to 5 carbon atoms, and still more preferably having 1 to 3 carbon atoms).

From the viewpoint of the suppression of volatilization and the degree of solubility, the molecular weight of the photopolymerization initiator used in the present invention is preferably in a range of 100 to 2000, more preferably in a range of 200 to 1800, and still more preferably in a range of 300 to 1500.

Hereinafter, specific examples of the photopolymerization initiator that can be used in the present invention will be described, but the present invention is not limited thereto.
[Chem. 14]
I-1
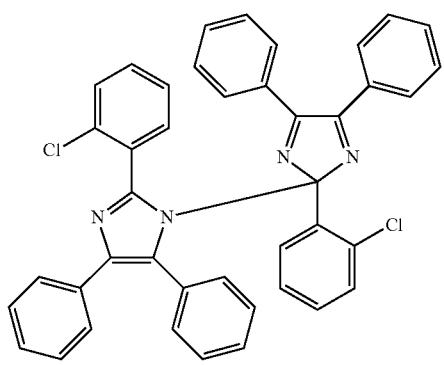
I-2
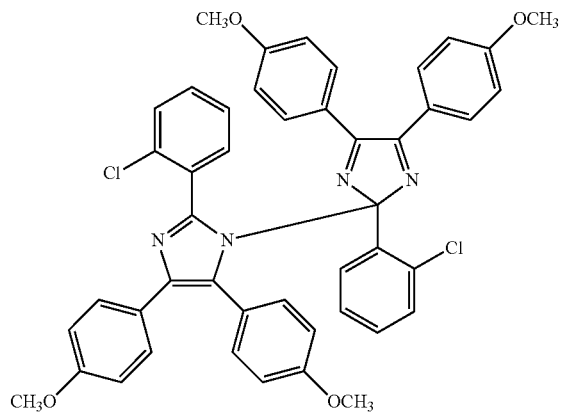
I-3
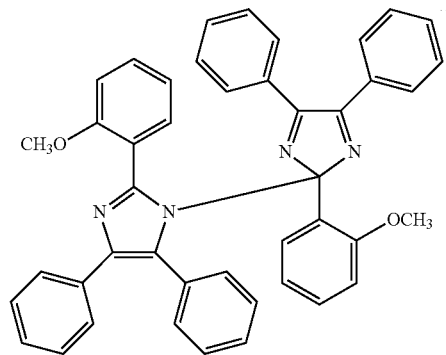

-continued
I-4
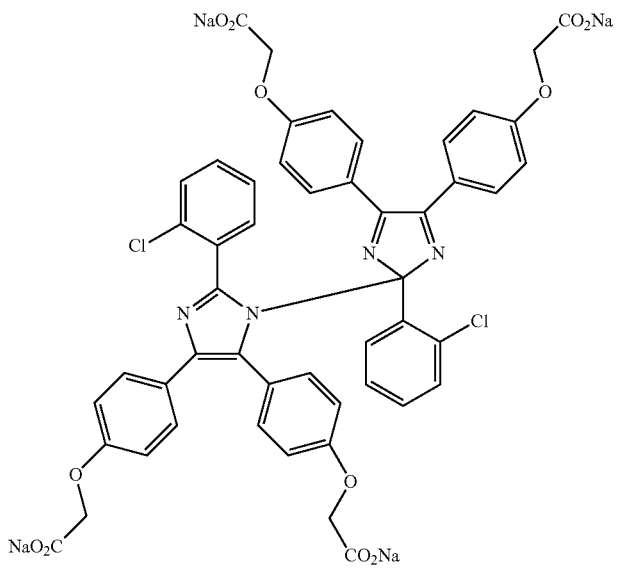
I-5
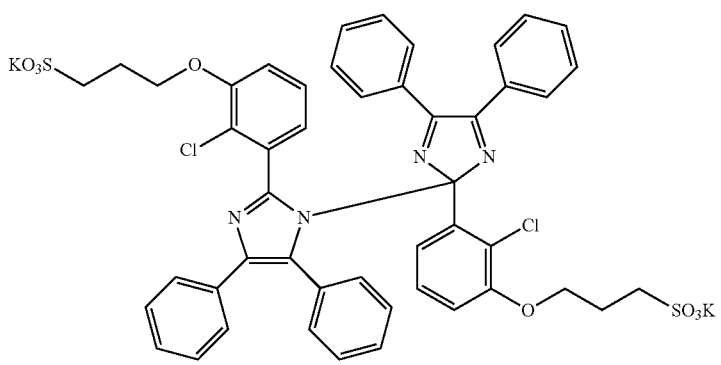
I-6
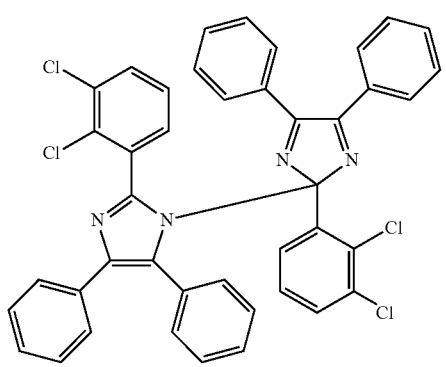
I-7
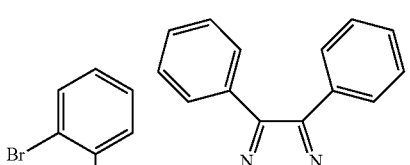
I-8
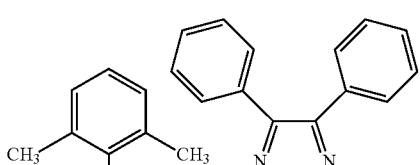

The content of the photopolymerization initiator in the ink composition used in the present invention is preferably in a range of 0.1 mass % to 40 mass %, more preferably in a range of 1 mass % to 30 mass %, and still more preferably in a range of 5 mass % to 20 mass % with respect to a total amount of 100 mass % of the solid content of the ink composition.

In addition, with respect to 100 parts by mass of the polymerizing compound, 0.1 parts by mass to 30 parts by mass of the photopolymerization initiator is preferably used, 1 part by mass to 20 parts by mass of the photopolymerization initiator is more preferably used, and 5 parts by mass to 15 parts by mass of the photopolymerization initiator is still more preferably used.

<(C) Hydrogen Donor>

In the present invention, the hydrogen donor having a structure in which a nitrogen atom is directly bonded to an aromatic ring, and (c-1) hydrogen donor in which the aromatic ring has an electron-withdrawing group or (c-2) hydrogen donor in which the nitrogen atom constitutes a hetero ring is used.

A radical species generated by the photopolymerization initiator draws a hydrogen atom, and thus turns into an active radical species, and thus the hydrogen donor used in the present invention acts as a polymerization accelerator or a chain transfer agent with respect to the polymerizing compound having an ethylenic unsaturated group.

The hydrogen donor used in the present invention has a structure in which a nitrogen atom is directly bonded to an aromatic ring. The aromatic ring may be an aromatic hydrocarbon ring or an aromatic hetero ring, but is preferably an aromatic hydrocarbon ring. The aromatic hydrocarbon ring may be a benzene ring or a poly benzene condensed ring (for example, a naphthalene ring or a phenanthrene ring), or the benzene ring or the poly benzene condensed ring to which a carbon ring, which is not an aromatic ring, for example, 3- to 7-membered cycloalkane or 5- to 7-membered cycloalkene is condensed. The aromatic hetero ring preferably includes a nitrogen atom, an oxygen atom, or a sulfur atom as a ring-constituting hetero atom. In addition, the aromatic hetero ring is preferably a 5- to 7-membered ring (more preferably a 5- or 6-membered ring), and may be the 5- to 7-membered ring to which an aromatic hydrocarbon ring, a carbon ring other than an aromatic ring (for example, cycloalkane or cycloalkene), or a hetero ring including an aromatic hetero ring (the preferable number of ring members and the preferable ring-constituting hetero atom are identical to those in the aromatic hetero ring described above) is condensed.

Here, the nitrogen atom directly bonded to the aromatic ring may be bonded to the aromatic ring through a single bond or a double bond. In addition, the remaining direct bond of the nitrogen atom bonded to the aromatic ring is linked with the aromatic ring through a linking group, and consequently, the hydrogen donor may have a structure in which a nitrogen-containing hetero ring is condensed to the aromatic ring.

The number of nitrogen atoms that are directly bonded to the aromatic ring is preferably in a range of 1 to 3, more preferably 1 or 2, and particularly preferably 1.

The pKa in water at room temperature (25° C.) of the hydrogen donor used in the present invention is preferably in a range of −5.0 to 8.0.

In the hydrogen donor used in the present invention, the aromatic ring to which the nitrogen atom is directly bonded may have a substituent. At least one of the substituents preferably has an electron-withdrawing group. At least one electron-withdrawing group has a positive Hammett σ value.

In the present invention, the "Hammett σ value" refers to a σp value in a case in which the position of the electron-withdrawing group is an o position or a p position with respect to the nitrogen atom, and a σm value in a case in which the position of the electron-withdrawing group is an m position with respect to the nitrogen atom. In addition, in a case in which the aromatic ring has a plurality of substituents, the total of the Hammett σ values (the σp value and σm value of the existing group) of these substituents is preferably zero or more.

The Hammett σ value (the σp value in a case in which the position of the electron-withdrawing group is an o position or a p position with respect to the nitrogen atom, and the σm value in a case in which the position of the electron-withdrawing group is an m position with respect to the nitrogen atom) of the electron-withdrawing group or the total of the Hammett σ values (the σp value and σm value of the existing group) of these substituents in a case in which the aromatic ring has a plurality of substituents is preferably in a range of 0.1 to 1.5, more preferably in a range of 0.2 to 1.0, and particularly preferably in a range of 0.3 to 0.8.

Examples of the electron-withdrawing group having a positive Hammett σp value include an aryl group, an alkenyl group, an alkynyl group, a carboxyl group, a sulfo group, an alkyl or arylsulfinyl group, a nitro group, halogen atoms, a fluoroalkyl group, a cyano group, an acyl group, an alkoxycarbonyl group, an aryloxy carbonyl group, a carbamoyl group, an alkylsulfonyl group, an arylsulfonyl group, an alkylsulfamoyl group, an arylsulfamoyl group, and an alkyl ammonio group. The electron-withdrawing group is preferably a group selected from halogen atoms, a fluoroalkyl group, a cyano group, an acyl group, an alkoxycarbonyl group, an aryloxy carbonyl group, a carbamoyl group, an alkylsulfonyl group, an arylsulfonyl group, an alkylsulfamoyl group, an arylsulfamoyl group, and an alkyl ammonio group, and, among them, is more preferably a group other than an alkoxycarbonyl group or an aryloxy carbonyl group of which the electron-withdrawing effect is weakened when the group is hydrolyzed, that is, a group selected from halogen atoms, a fluoroalkyl group, a cyano group, an acyl group, a carbamoyl group, an alkylsulfonyl group, an arylsulfonyl group, an alkylsulfamoyl group, an arylsulfamoyl group, and an alkyl ammonio group.

Examples of the electron-withdrawing group having a positive Hammett σm value include a hydroxyl group, an alkoxy group, an alkenyloxy group, an aryloxy group, a trialkylsilyloxy group, a hydroxyalkyl group, and electron-withdrawing groups having a positive Hammett σp value, and the electron-withdrawing group having a positive Hammett σm value is preferably a group selected from an alkoxy group, an aryloxy group, a hydroxyalkyl group, halogen atoms, a fluoroalkyl group, a cyano group, an acyl group, an alkoxycarbonyl group, an aryloxy carbonyl group, a carbamoyl group, an alkylsulfonyl group, an arylsulfonyl group, an alkylsulfamoyl group, and an arylsulfamoyl group, and more preferably a group selected from an alkoxy group, halogen atoms, a fluoroalkyl group, a cyano group, an acyl group, a carbamoyl group, an alkylsulfonyl group, an arylsulfonyl group, an alkylsulfamoyl group, and an arylsulfamoyl group.

Among substituents that the aromatic ring may have, examples of substituents other than the electron-withdrawing group described above include an alkyl group, an alkoxy group, an aryloxy group, an alkylthio group, an arylthio group, a hydroxyl group, an amino group (including an amino group, an alkylamino group, an arylamino group, and a hetero ring amino group).

Among them, an alkyl group and an alkoxy group are preferred, and the preferable aspects of these groups are identical to the preferable aspects of the alkyl group and the alkoxy group in $R^1$ to $R^{30}$ in Formula (1). In addition, the alkyl group and the alkoxy group may further have a substituent.

The hydrogen donor used in the present invention is preferably one or more types of compounds represented by Formula (2) or (3) described below. Among them, the hydrogen donor is more preferably one or more types of compounds represented by Formula (2) described below.

[Chem. 20]

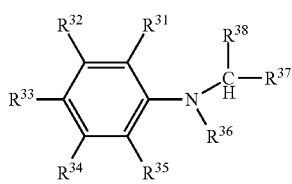

FORMULA (2)

In Formula (2), each of $R^{31}$ to $R^{35}$ represents a hydrogen atom or a substituent. Here, at least one of $R^{31}$ to $R^{35}$ is an electron-withdrawing group. $R^{36}$ represents a hydrogen atom, an alkyl group, or an aryl group. Each of $R^{37}$ and $R^{38}$ represents a hydrogen atom or an alkyl group.

[Chem. 21]

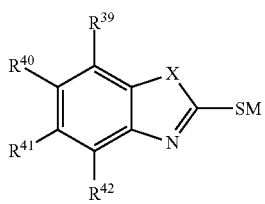

FORMULA (3)

In Formula (3), each of $R^{39}$ to $R^{42}$ represents a hydrogen atom or a substituent. X represents an oxygen atom, a sulfur atom, or a nitrogen atom having a substituent. M represents a hydrogen atom or an alkali metal.

In a case in which M is an alkali metal, —SM changes to —SH under acidic conditions, and functions as the hydrogen donor. Therefore, under neutral or alkaline conditions, the polymerization reaction does not easily proceed, and therefore it is possible to further improve the preservation stability of the ink composition.

Examples of the substituent that can be employed as $R^{31}$ to $R^{35}$ include substituents that the alkyl group and the alkoxy group may have in $R^1$ to $R^{30}$ in Formula (1).

The substituent that can be employed as $R^{31}$ to $R^{35}$ is preferably an alkyl group, an alkoxy group, or an electron-withdrawing group, and the preferable aspects of the alkyl group and the alkoxy group are identical to the preferable aspects of the alkyl group and the alkoxy group in $R^1$ to $R^{30}$ in Formula (1). In addition, the electron-withdrawing group is preferably the electron-withdrawing group that has been described as the electron-withdrawing group that the hydrogen donor described above may have.

In a case in which each of $R^{36}$ to $R^{38}$ is an alkyl group, the preferable aspects thereof are identical to the preferable aspects of the alkyl group in $R^1$ to $R^{30}$ in Formula (1).

In a case in which $R^{36}$ is an aryl group, the number of carbon atoms is preferably in a range of 6 to 12, and a phenyl group that may have a substituent is more preferred. Examples of the substituent that the phenyl group may have include the substituents that the alkyl group and the alkoxy group may have in $R^1$ to $R^{30}$ in Formula (1).

Three or four of $R^{31}$ to $R^{35}$ are preferably hydrogen atoms, and four of them are more preferably hydrogen atoms.

$R^{36}$ is preferably an alkyl group, and more preferably an alkyl group having a hydrogen bond at an α position.

$R^{37}$ and $R^{38}$ are preferably hydrogen atoms or alkyl groups having 1 to 3 carbon atoms, and are particularly preferably hydrogen atoms.

In the compound represented by Formula (2), $R^{33}$ is particularly preferably a halogen atom (preferably a fluorine atom or a chlorine atom), a fluoroalkyl group (preferably trifluoromethyl), an alkoxycarbonyl group (preferably methoxycarbonyl or ethoxycarbonyl), a carbamoyl group (preferably carbamoyl, N-methylcarbamoyl, or N,N-dimethylcarbamoyl), or a cyano group.

In the present invention, the molecular weight of the hydrogen donor represented by Formula (2) is preferably in a range of 50 to 1500, more preferably in a range of 80 to 1000, and still more preferably in a range of 100 to 500 from the viewpoint of the suppression of volatilization and the degree of solubility.

Hereinafter, specific examples of the compound represented by Formula (2) will be described, but the present invention is not limited thereto.

[Chem. 22]

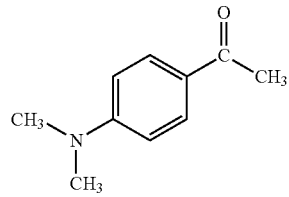

A-1

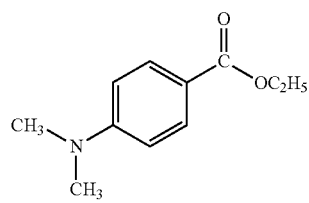

A-2

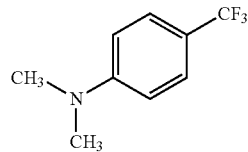

A-3

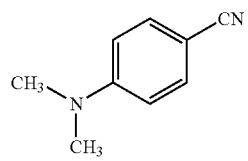

A-4

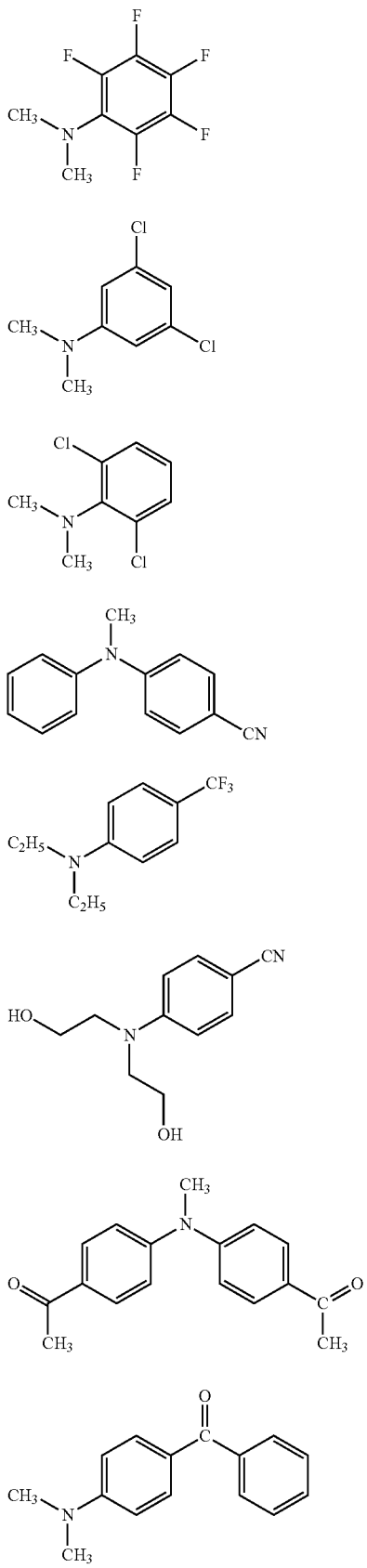

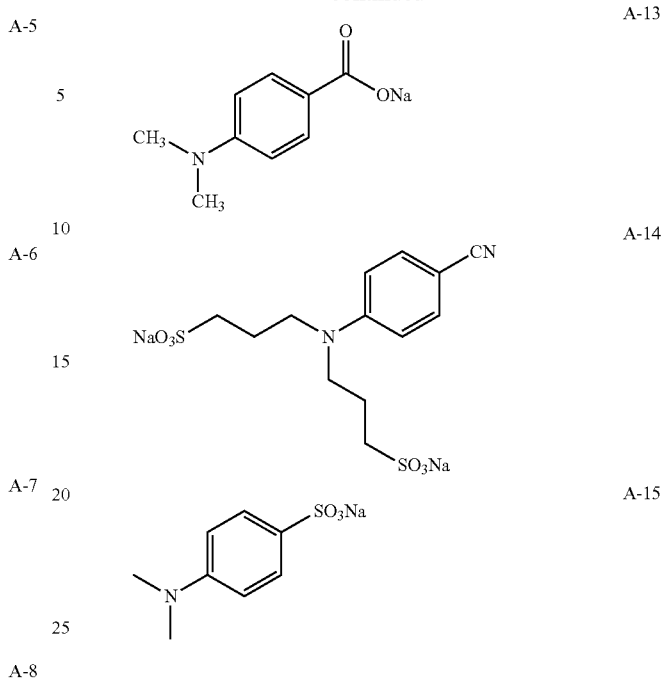

In Formula (3), each of $R^{39}$ to $R^{42}$ represents a hydrogen atom or a substituent, and examples of the substituent include substituents that the alkyl group and the alkoxy group, which $R^1$ to $R^{30}$ in Formula (1) may employ, may have. A substituent that $R^{39}$ to $R^{42}$ may employ is preferably a halogen atom, a cyano group, an amino group, an ammonio group, a carbamoyl group, an alkyl group (preferably having 1 to 5 carbon atoms, more preferably having 1 to 3 carbon atoms, and still more preferably trifluoromethyl) or an alkoxy group (an alkoxy group preferably having 1 to 5 carbon atoms, and more preferably having 1 to 3 carbon atoms).

In addition, each of $R^{39}$ and $R^{42}$ is also preferably a hydrogen atom or an electron-withdrawing group that the above-described hydrogen donor may have. For example, a preferable aspect is that one of $R^{39}$ and $R^{42}$ is an electron-withdrawing group, and all the rest of them are hydrogen atoms. In addition, an aspect in which all of $R^{39}$ and $R^{42}$ are hydrogen atoms is also preferred.

In a case in which M in Formula (3) is an alkali metal, M is preferably sodium or potassium.

In the present invention, from the viewpoint of the suppression of volatilization and solubility, the molecular weight of the hydrogen donor represented by Formula (3) is preferably in a range of 50 to 1500, more preferably in a range of 80 to 1000, and still more preferably in a range of 100 to 500.

Hereinafter, specific examples of the compound represented by Formula (3) will be described, but the present invention is not limited thereto. In the following formulae, M represents a hydrogen atom or an alkali metal.

[Chem. 23]

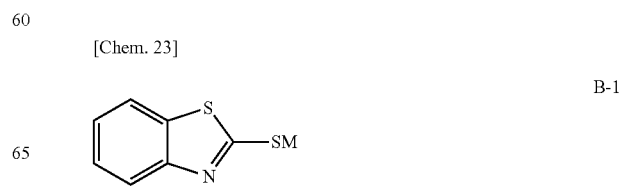

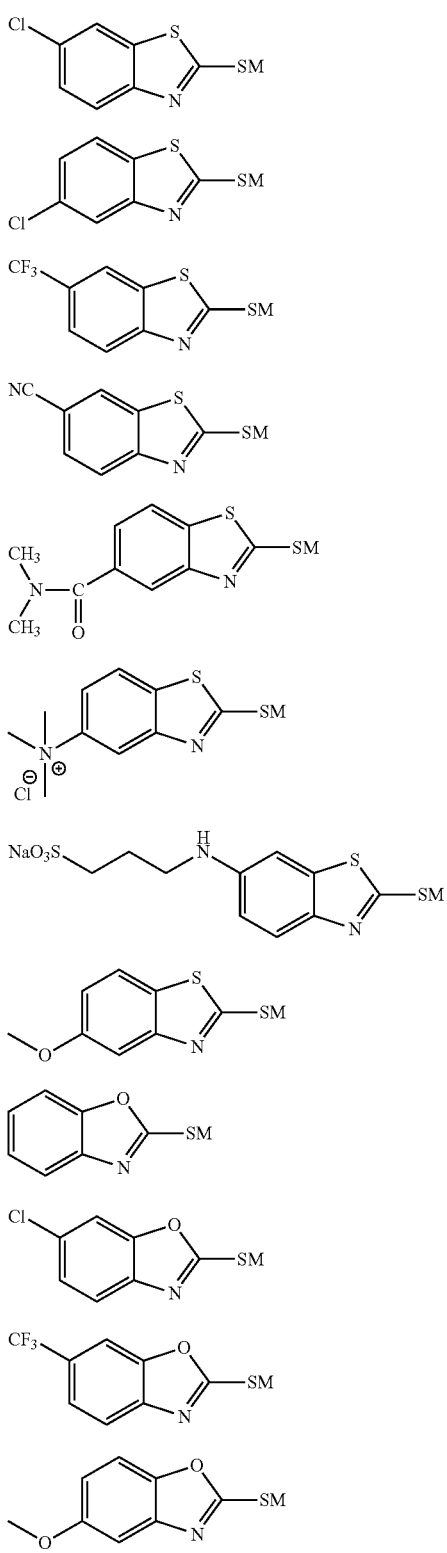

B-2
B-3
B-4
B-5
B-6
B-7
B-8
B-9
B-10
B-11
B-12
B-13

The content of the hydrogen donor in the ink composition used in the present invention is preferably in a range of 0.1 mass % to 40 mass %, more preferably in a range of 1 mass % to 30 mass %, and still more preferably in a range of 1 mass % to 20 mass % with respect to a total amount of 100 mass % of the solid content of the ink composition.

The content of the hydrogen donor in the ink composition used in the present invention is preferably in a range of 5 mass % to 1500 mass %, more preferably in a range of 10 mass % to 1000 mass %, and still more preferably in a range of 20 mass % to 500 mass % with respect to 100 mass % of an amount of the photopolymerization initiator in the composition.

<Other Components>

In addition to the polymerizing compound having an ethylenic unsaturated group, the photopolymerization initiator, and the hydrogen donor, the ink composition used in the present invention may include, as necessary, other components, for example, one or more selected from trialkylamine, a colorant, a medium, and a dispersing agent.

—(D) Trialkylamine—

When (D) trialkyamine is added to the ink composition used in the present invention, it is possible to further increase the photopolymerization efficiency. The mechanism is not clear, but is considered as described below.

In (B) the photopolymerization initiator having the above-described component, a bond that couples two imidazole rings is cut by the radiation of light, and the biimidazole structure is disassociated into two imidazole structural units. In a case in which trialkylamine is not present, an imidazole ring in the disassociated imidazole structural unit draws an electron from (C) the hydrogen donor having the above-described component, and the hydrogen donor is radicalized. This radical initiates the polymerization reaction of (A) the polymerizing compound having the above-described component.

Meanwhile, when oxygen is present in the reaction system, the imidazole ring in the disassociated imidazole structural unit is capable of bringing in an oxygen molecule so as to generate an oxygen radical (—O—O.). However, this oxygen radical is not capable of drawing oxygen from (C) the hydrogen donor having the above-described component. On the other hand, the oxygen radical is capable of drawing a hydrogen atom of trialkylamine. Therefore, in a case in which trialkylamine is present, trialkylamine donates hydrogen to the oxygen radical, and thus is radicalized. This trialkylamine radical draws hydrogen from (C) the hydrogen donor having the above-described component. Therefore, it is considered that the above-described component (C) is radicalized, and initiates the polymerization reaction of the polymerizing compound.

Trialkylamine that can be used in the present invention is represented by Formula (TA) described below.

$$N(R^{ta})_3 \qquad (TA)$$

In Formula (TA), $R^{ta}$ represents a substituted or unsubstituted alkyl group. The number of carbon atoms in the alkyl group is preferably in a range of 1 to 10, more preferably in a range of 1 to 5, and still more preferably in a range of 1 to 3. There is no particular limitation regarding a substituent that $R^{ta}$ may have, and examples thereof include a hydroxyl group, an alkoxy group, a carboxyl group, an amide group, and an amino group, and a hydroxyl group is more preferred.

Specific examples of trialkylamine that can be used in the present invention include N-methyldiethanolamine, triethylamine, triisopropanolamine, triethanolamine, N,N,N',N'-tetramethylethylenediamine, N,N-dimethylglycine, 2-(dimethylamino)ethanol, 2-(diethylamino)ethanol, and 2-[2-(dimethylamino)ethoxy]ethanol, and, among them, it is possible to preferably use N-methyldiethanolamine, triethylamine, or triisopropanolamine.

The content of trialkylamine in the ink composition used in the present invention is preferably in a range of 0.1 parts by mass to 20 parts by mass, more preferably in a range of 0.5 parts by mass to 10 parts by mass, and still more preferably in a range of 1 part by mass to 5 parts by mass with respect to 100 parts by mass of a total amount of the solid content of the ink composition.

The content of trialkylamine in the ink composition used in the present invention is preferably in a range of 0.1 parts by mass to 200 parts by mass, more preferably in a range of 1 part by mass to 150 parts by mass, and still more preferably in a range of 10 parts by mass to 100 parts by mass with respect to 100 parts by mass of an amount of the photopolymerization initiator in the composition.

—(E) Colorant—

The ink composition used in the present invention preferably includes (E) a colorant.

The ink composition of the present invention can be used not only for the formation of a monochromatic image but also for the formation of a polychromatic image (for example, a full color image), and it is possible to form an image by selecting one or more desired colors. In a case in which a full color image is formed, the ink composition can be used as, for example, a magenta color tone ink, a cyan color tone ink, and a yellow color tone ink. In addition, furthermore, the ink composition can be used as a black color tone ink.

In addition, the ink composition of the present invention can be used as ink compositions of red (R), green (G), blue (B), and white (W) color tones other than yellow (Y), magenta (M), cyan (C), and black (K) color tones or ink compositions of characteristic colors in the so-called printing field.

The ink compositions of the respective color tones described above can be prepared by changing the hues of colorants (for example, pigments) as desired.

In the ink composition of the present invention, it is possible to use well-known dyes, pigments, and the like with no limitation as the colorant. From the viewpoint of the colorability of a formed image, a colorant that is rarely or not easily dissolved in water is preferred. Specific examples thereof include a variety of pigments, disperse dyes, oil-soluble dyes, coloring agents that form a J aggregate, and the like, and when light resistance is taken into account, pigments are more preferred.

The type of a pigment used in the ink composition of the present invention is not particularly limited, and an ordinary organic or inorganic pigment can be used.

Examples of the organic pigment include azo pigments, polycyclic pigments, dye chelate, nitro pigments, nitroso pigments, aniline black, and the like. Among them, azo pigments, polycyclic pigments, and the like are more preferred. Examples of the azo pigments include azo lake, insoluble azo pigments, condensed azo pigments, chelate azo pigments, and the like. Examples of the polycyclic pigments include phthalocyanine pigments, peryline pigments, perinone pigments, anthraquinone pigments, quinacridone pigments, dioxazine pigments, indigo pigments, thioindigo pigments, isoindolinone pigments, quinophthalone pigments, and the like. Examples of the dye chelate include basic dye-type chelate, acidic dye-type chelate, and the like.

Examples of the inorganic pigment include titanium oxide, iron oxide, calcium carbonate, barium sulfate, aluminum hydroxide, barium yellow, cadmium red, chrome yellow, carbon black, and the like. Among them, carbon black is particularly preferred. Meanwhile, examples of carbon black include carbon black manufactured using a well-known method such as a contact method, a furnace method, or a thermal method.

Specific examples of pigments that can be used in the present invention include the pigments described in paragraphs 0142 to 0145 in JP2007-100071A.

In a case in which a dye is used as a coloring component in the present invention, it is possible to use a substance obtained by holding a dye in a water-insoluble carrier as the colorant. A well-known dye can be used with no particular limitation as the dye, and, for example, the dyes described in JP2001-115066A, JP2001-335714A, and JP2002-249677A can also be preferably used in the present invention. In addition, as the carrier, it is possible to use with no particular limitation an inorganic material, an organic material, or a complex material thereof as long as the material is insoluble or not easily dissolved in water. Specifically, the carriers described in JP2001-181549A, JP2007-169418A, and the like can also be preferably used in the present invention.

The carrier holding a dye (the colorant) can be singly used or, if necessary, jointly used with a dispersing agent. As the dispersing agent, it is possible to preferably use dispersing agents described below.

The colorant may be singly used, or a combination of a plurality of the colorants may be used.

From the viewpoint of color density, granularity, ink stability, and discharging reliability, the content of the colorant (particularly the pigment) in the ink composition is preferably 1 mass % to 25 mass %, and more preferably in a range of 5 mass % to 20 mass % with respect to the total mass of the ink composition. In addition, the ink composition of the present invention is capable of producing sufficient curing properties even in a case in which the content of the colorant in the ink composition is as relatively high as 6 mass % to 25 mass %.

—Medium—

The ink composition of the present invention may include a medium (a solvent), and any of an organic medium and a aqueous medium can be included. An aqueous medium contains at least water, and preferably contains at least one type of water-soluble organic solvents as necessary.

Water used in the aqueous medium is preferably water containing no ionic impurities such as ion exchange water or distilled water.

Examples of the water-soluble organic solvent include alcohol, ketone, ether compounds, amide compounds, nitrile compounds, and sulfone compounds. Among them, examples of the alcohol include ethanol, isopropanol, n-butanol, t-butanol, isobutanol, diacetone alcohol, and ethylene glycol. Examples of the ketone include acetone, methyl ethyl ketone, diethyl ketone, and methyl isobutyl ketone. Examples of the ether compounds include dibutyl ether, tetrahydrofuran, and dioxane. Examples of the amide compounds include dimethyl formamide and diethyl formamide. Examples of the nitrile compounds include acetonitrile. Examples of the sulfone compounds include dimethyl sufoxide, dimethyl sulfone, and sulfolane.

The content of the medium in the ink composition can be appropriately selected depending on purpose, and generally, the content in the ink composition is preferably in a range of 10 mass % to 95 mass %, and more preferably in a range of 30 mass % to 90 mass %.

—Dispersing Agent—

In a case in which the ink composition of the present invention is an aqueous composition, and the colorant is a pigment, it is preferable to constitute coloring particles dispersed in the aqueous medium using a dispersing agent (hereinafter, referred to simply as "coloring particles").

The dispersing agent may be any of a polymer dispersing agent and a low-molecular surfactant-type dispersing agent. In addition, the polymer dispersing agent may be any of a water-soluble polymer dispersing agent and a water-insoluble polymer dispersing agent. In the present invention, from the viewpoint of dispersion stability and discharging properties in a case in which the dispersing agent is applied to an ink jet method, a water-insoluble polymer dispersing agent is preferred.

The water-insoluble polymer dispersing agent (hereinafter, referred to simply as "dispersing agent" in some cases) is a water-insoluble polymer, and a well-known water-insoluble polymer dispersing agent of the related art can be used with no particular limitation as long as the dispersing agent is capable of dispersing the pigment. The water-insoluble polymer dispersing agent can be constituted by, for example, including both a hydrophobic constitutional unit and a hydrophilic constitutional unit.

Here, examples of a monomer constituting the hydrophobic constitutional unit include a styrene-based monomer, alkyl (meth)acrylate, aromatic group-containing (meth)acrylate, and the like.

In addition, a monomer constituting the hydrophilic constitutional unit is not particularly limited as long as the monomer has a hydrophilic group. Examples of the hydrophilic group include a nonionic group, a carboxyl group, a sulfonic acid group, a phosphoric acid group, and the like. Meanwhile, examples of the nonionic group include a hydroxyl group, an amide group (with an unsubstituted nitrogen atom), groups derived from an alkylene oxide polymer (for example, polyethylene oxide, polypropylene oxide, and the like), groups derived from sugar alcohol, and the like.

From the viewpoint of dispersion stability, the hydrophilic constitutional unit preferably has at least a carboxyl group, and also preferably includes both a nonionic group and a carboxyl group.

Specific examples of the water-insoluble polymer dispersing agent include styrene-(meth)acrylic acid copolymers, styrene-(meth)acrylic acid-(meth)acrylic acid ester copolymers, (meth)acrylic acid ester-(meth)acrylic acid copolymers, polyethylene glycol (meth)acrylate-(meth)acrylic acid copolymers, styrene-maleic acid copolymers, and the like.

From the viewpoint of the dispersion stability of the pigment, the water-insoluble polymer dispersing agent is preferably a vinyl polymer having a carboxyl group, and more preferably a vinyl polymer which includes at least a constitutional unit derived from an aromatic group-containing monomer as the hydrophobic constitutional unit and a constitutional unit having a carboxyl group as the hydrophilic constitutional unit.

In addition, from the viewpoint of the dispersion stability of the pigment, the weight-average molecular weight of the water-insoluble polymer dispersing agent is preferably in a range of 3,000 to 200,000, more preferably in a range of 5,000 to 100,000, still more preferably in a range of 5,000 to 80,000, and particularly preferably in a range of 10,000 to 60,000.

From the viewpoint of the dispersibility, ink coloring properties, and dispersion stability of the pigment, the content of the dispersing agent in the coloring particles is preferably in a range of 10 mass % to 90 mass %, more preferably in a range of 20 mass % to 70 mass %, and particularly preferably in a range of 30 mass % to 50 mass % with respect to 100 mass % of the pigment.

The content of the dispersing agent in the coloring particles is preferably within the above-described range because the pigment is covered with an appropriate amount of the dispersing agent, and there is a tendency that coloring particles having small particle diameters and excellent temporal stability are easily obtained.

The coloring particles can be obtained in a form of a coloring particle-dispersed substance by, for example, dispersing a mixture of the pigment, the dispersing agent, if necessary, a solvent (preferably an organic solvent), and the like using a disperser.

The coloring particle-dispersed substance can be manufactured by, for example, providing a step of adding an aqueous solution including a basic substance to a mixture of the pigment, the water-insoluble polymer dispersing agent, and an organic solvent that dissolves or disperses the dispersing agent (a mixing and hydration step), and then a step of removing the organic solvent (a solvent removal step). As a result, it is possible to produce a coloring particle-dispersed substance having excellent preservation stability in which the pigment is finely dispersed.

The organic solvent needs to be capable of dissolving or dispersing the water-insoluble polymer dispersing agent, and preferably has a certain degree of affinity to water in addition to the above-described characteristic. Specifically, the degree of solubility in water at 20° C. is preferably in a range of 10 mass % to 50 mass %.

The basic substance is used to neutralize an anionic group (preferably a carboxyl group) which is, in some cases, included in the water-insoluble polymer. There is no particular limitation regarding the degree of neutralization of the anionic group. Regarding the liquid properties of the finally obtained coloring particle-dispersed substance, generally, for example, the pH is preferably in a range of 4.5 to 10. It is also possible to determine the pH using the desired degree of neutralization of the water-insoluble polymer.

Preferable examples of the organic solvent include the water-soluble organic solvents described in the above-described "medium" section that the ink composition may have. Among them, isopropanol, acetone, and methyl ethyl ketone are preferred, and methyl ethyl ketone is particularly preferred. The organic solvent may be singly used, or a plurality of organic solvents may be jointly used.

There is no particular limitation regarding a method for removing the organic solvent in a step of manufacturing the coloring particle-dispersed substance, and the organic solvent can be removed using a well-known method such as distillation at reduced pressure.

In the ink composition of the present invention, one type of the coloring particles may be singly used, or a combination of two or more types of the coloring particles may be used.

The volume-average particle diameter of the colorant (or the coloring particles) in the present invention is preferably in a range of 10 nm to 200 nm, more preferably in a range of 10 nm to 150 nm, and still more preferably in a range of 10 nm to 100 nm. When the volume-average particle diameter is 200 nm or less, the color reproducibility becomes favorable, and, in the case of the ink jet method, the droplet strike characteristic becomes favorable. In addition, when the volume-average particle diameter is 10 nm or more, the light resistance becomes favorable.

In addition, there is no particular limitation regarding the particle diameter distribution of the colorant (or the coloring particles), and the particle diameter distribution may be any of a wide particle diameter distribution and a monodispersed particle diameter distribution. In addition, a mixture of two or more types of colorants having a monodispersed particle diameter distribution may be used.

The volume-average particle diameter and particle diameter distribution of the colorant (or the coloring particles) can be measured using, for example, a light scattering method.

—Other Polymerization Initiators—

The ink composition used in the present invention may include polymerization initiators other than the compound represented by Formula (1) in the present invention (hereinafter, referred to as "other polymerization initiators") as necessary.

<Properties of the Ink Composition>

The surface tension (25° C.) of the ink composition used in the present invention is preferably in a range of 20 mN/m to 60 mN/m, more preferably in a range of 20 mN/m to 45 mN/m, and still more preferably in a range of 25 mN/m to 40 mN/m.

The surface tension is measured using an automatic surface tensiometer CBVP-Z (manufactured by Kyowa Interface Science Co., Ltd.) under a condition in which the ink composition is at 25° C.

In addition, the viscosity of the ink composition of the present invention at 25° C. is preferably in a range of 1.2 mPa·s to 15.0 mPa·s, more preferably in a range of 2 mPa·s to less than 13 mPa·s, and still more preferably in a range of 2.5 mPa·s to less than 10 mPa·s.

The viscosity is measured using a VISCOMETER TV-22 (manufactured by Told Sangyo Co., Ltd.) under a condition in which the ink composition is at 25° C.

From the viewpoint of the stability of the ink composition, the pH of the ink composition is preferably in a range of 6 to 11. In the case of an ink set described below, the ink composition is preferably aggregated at a high speed through the contact with an acid treatment agent, and therefore the pH is more preferably in a range of 7 to 10, and still more preferably in a range of 7 to 9.

[Ink Set]

An ink set of the present invention includes at least a part of the above-described ink composition and an acid treatment agent which is capable of forming an aggregate through the contact with the ink composition.

When an image is formed using the ink composition and the acid treatment agent, it is possible to form an image having favorable image qualities, high curing sensitivity, and excellent blocking resistance.

Hereinafter, the acid treatment agent constituting the ink set will be described.

<Acid Treatment Agent>

The acid treatment agent constituting the ink set is constituted by including at least an acidic compound and, if necessary, other components. Examples of the other components include a water-soluble organic solvent or a cationic polymer.

The acid treatment agent used in the present invention is generally an aqueous solution.

[Acidic Compound]

The acidic compound used in the acid treatment agent is capable of aggregating (immobilizing) the ink composition when coming into contact with the ink composition on a recording medium, and functions as an immobilization agent. For example, when the ink composition lands on a recording medium (preferably coated paper) in a state in which the acid treatment agent is supplied to the recording medium, it is possible to aggregate components in the ink composition, and to immobilize the ink composition on the recording medium.

In addition, when the acid treatment agent is left on the recording medium, it is possible to improve the polymerization efficiency of the ink composition which landed on the recording medium.

Examples of the acidic compound include sulfuric acid, hydrochloric acid, nitric acid, phosphoric acid, polyacrylic acid, acetic acid, glycolic acid, malonic acid, malic acid, maleic acid, ascorbic acid, succinic acid, glutaric acid, fumaric acid, citric acid, tartaric acid, lactic acid, sulfonic acid, orthophosphoric acid, metaphosphoric acid, pyrrolidone carboxylic acid, pyronecarboxylic acid, pyrrolecarboxylic acid, furancarboxylic acid, pyridinecarboxylic acid, coumaric acid, thiophenecarboxylic acid, nicotinic acid, oxalic acid, and benzoic acid. From the viewpoint of satisfying both the suppression of volatilization and the degree of solubility in a solvent, the acidic compound is preferably an acid having a molecular weight in a range of 35 to 1000, more preferably an acid having a molecular weight in a range of 50 to 500, and particularly preferably an acid having a molecular weight in a range of 50 to 200. In addition, from the viewpoint of satisfying both the prevention of ink bleeding and photocuring properties, an acid having a pKa (25° C. in water) in a range of −10 to 7 is preferred, an acid having a pKa in a range of 1 to 7 is more preferred, and an acid having a pKa in a range of 1 to 5 is particularly preferred.

Among them, a highly water-soluble acid is preferred. In addition, from the viewpoint of immobilizing the entire ink through a reaction with the ink composition, a trivalent or lower acid is preferred, and a divalent or trivalent acid is particularly preferred.

In the present invention, the acidic compound may be singly used, or two or more acidic compounds may be jointly used.

In a case in which the acid treatment agent is an aqueous solution, the pH (25° C.) of the acid treatment agent is preferably in a range of 0.1 to 6.8, more preferably in a range of 0.5 to 6.0, and still more preferably in a range of 0.8 to 5.0.

The content of the acidic compound in the acid treatment agent is preferably 40 mass % or less, more preferably in a range of 15 mass % to 40 mass %, still more preferably in a range of 15 mass % to 35 mass %, and particularly preferably in a range of 20 mass % to 30 mass %. When the content of the acidic compound in the acid treatment agent is set in a range of 15 mass % to 40 mass %, it is possible to more efficiently immobilize the components in the ink composition.

The amount of the acid compound supplied to a recording medium is not particularly limited as long as the ink composition is aggregated; however, from the viewpoint of ease of immobilizing the ink composition, the amount is preferably in a range of 0.5 g/m$^2$ to 4.0 g/m$^2$, and more preferably in a range of 0.9 g/m$^2$ to 3.75 g/m$^2$.

[Photopolymerization Method]

A photopolymerization method of the present invention is a method for photopolymerizing the above-described ink composition under acidic conditions. This photopolymerization enables the formation of a more accurate ink image. That is, the photopolymerization method of the present invention is a preferable image-forming method. During photopolymerization, a step of radiating an active energy ray described below is preferably applied.

<Acidic Conditions>

The acidic conditions in the photopolymerization method of the present invention refers to a reaction system in an acidic state in which at least one type of acid is present in a solution. The content of the acid in the reaction system is not particularly limited as long as the polymerization reaction of the polymerizing compound proceeds; however, when the viewpoint of ease of immobilization through the aggregation of the ink composition is taken into account, the content is preferably in a range of 0.1 mass % to 1000 mass %, more preferably 1 mass % to 500 mass %, and still more preferably in a range of 10 mass % to 300 mass % with respect to a total amount of 100 mass % of the solid content of the ink composition. In a case in which the reaction system is an aqueous solution, under the acidic conditions, the pH is preferably in a range of 1 to less than 7, more preferably 2 to less than 7, and still more preferably in a range of 3 to less than 7. Examples of the acid include the acids exemplified as the "acidic compound" described above.

<Formation of Image>

An image can be formed using the photopolymerization method of the present invention. The formation of the image preferably includes at least an acid treatment step of supplying the acid treatment agent, which is a part of the ink set, onto a recording medium, an ink-supplying step of supplying the ink composition onto the recording medium, thereby forming an image, and a photopolymerization step of photopolymerizing the polymerizing compound in the formed image through light radiation.

—Recording Medium—

There is no particular limitation regarding the recording medium used in the image-forming method of the present invention, and it is possible to use ordinary printing paper which is used for ordinary offset printing and the like and includes cellulose as a main body, such as so-called high-quality paper, coated paper, and art paper. On the ordinary printing paper including cellulose as a main body, when an image is recorded using an ordinary ink jet method in which an aqueous ink is used, the absorption and drying of ink is relatively slow, the transfer of a color material is likely to occur after the strike of ink, and the image qualities are likely to degrade. However, in a case in which the above-described ink composition or ink set is used, the transfer of a color material is suppressed, and a high-quality image having excellent color density and hue can be recorded.

Commercially available ordinary paper can be used as the recording medium, and examples thereof include "OK Prince High Quality" manufactured by Oji Paper Co., Ltd., "SHIRAOI" manufactured by Nippon Paper Industries Co., Ltd., high-quality paper (A) such as "NEW NPI High Quality" manufactured by Nippon Paper Industries Co., Ltd., high-quality coated paper such as "SILVER DIAMOND" manufactured by Nippon Paper Industries Co., Ltd., fine coated paper such as "OK EVERLIGHT COAT" manufactured by Oji Paper Co., Ltd. and "AURORA S" manufactured by Nippon Paper Industries Co., Ltd., light-weight coated paper (A3) such as "OK COAT L" manufactured by Oji Paper Co., Ltd. and "AURORA L" manufactured by Nippon Paper Industries Co., Ltd., coated paper (A2, B2) such as "OK TOP COAT+" manufactured by Oji Paper Co., Ltd. and "AURORA COAT" manufactured by Nippon Paper Industries Co., Ltd., art paper (A1) such as "OK KANETO+" manufactured by Oji Paper Co., Ltd. and "TOKUBISHI ART" manufactured by Mitsubishi Paper Mills Limited, and the like. In addition, it is also possible to use a variety of photographic paper for ink jet recording.

Among the recording media, so-called coated paper, which is used for ordinary offset printing, is preferred. The coated paper is paper obtained by applying a coating material to the surface of high-quality paper, alkaline paper, or the like, which includes cellulose as a main body, and is, generally, not subjected to a surface treatment, thereby providing a coated layer. The coated paper is likely to cause a problem in terms of qualities such as the luster or wear resistance of an image in the formation of the image by an ordinary aqueous ink jet; however, in a case in which the above-described ink composition or ink set is used, luster variation is suppressed, and an image having favorable shine properties and scratch resistance can be obtained. Particularly, coated paper including original paper and a coated layer including kaolin and/or heavy calcium bicarbonate is preferably used. More specifically, art paper, coated paper, light-weight coated paper, or fine coated paper is more preferred.

Among them, from the viewpoint of a strong effect that suppresses the transfer of a color material and the obtainment of a high-quality image having more favorable color density and hue than before, the absorption coefficient Ka of the recording medium is preferably in a range of 0.05 $mL/m^2 \cdot ms^{1/2}$ to 0.5 $mL/m^2 \cdot ms^{1/2}$, more preferably in a range of 0.1 $mL/m^2 \cdot ms^{1/2}$ to 0.4 $mL/m^2 \cdot ms^{1/2}$, and still more preferably in a range of 0.2 $mL/m^2 \cdot ms^{1/2}$ to 0.3 $mL/m^2 \cdot ms^{1/2}$.

The absorption coefficient Ka of water is identical to that described in JAPAN TAPPI's paper and pulp testing method No. 51:2000 (published by JAPAN TAPPI), and specifically, the absorption coefficient Ka is computed from the difference in the amount of water transferred between a contact duration 100 ms and a contact duration 900 ms using an automatic scanning absorptometer KM500Win (manufactured by Kumagai Riki Kogyo Co., Ltd.).

—Acid Treatment Step (Acid Treatment Agent-supplying Step)—

In the acid treatment step, the acid treatment agent included in the ink set is supplied onto the recording medium. For the supply of the acid treatment agent (aqueous solution) to the recording medium, a well-known liquid-supplying method can be used with no particular limitation, and it is possible to select an arbitrary method such as spray coating, coating by a coating roller or the like, supply by the ink jet method, or immersion.

Specific examples thereof include size press methods represented by a horizontal size press method, a roll coater method, a calendar size press method, and the like; size press methods represented by an air knife coater method and the like; a knife coater method represented by an air knife coater method and the like; transfer roll coater methods such as a gate roll coater method and the like, roll coater methods represented by a direct roll coater method, a reverse roll coater method, a squeeze roll coater method, or the like; a bill blade coater method and a short dwell coater method; blade coater methods represented by a two stream coater method and the like; bar coater methods represented by a rod bar coater method and the like; cast coater methods; gravure coater methods; curtain coater methods; die coater methods; brush coater methods; transfer methods, and the like.

In addition, it is also possible to use a method in which the acid treatment agent is applied by controlling the coating amount using a coating apparatus equipped with a liquid amount restriction member such as the coating apparatus described in JP1998-230201A (JP-H10-230201A).

Regarding the region in which the acid treatment agent is supplied, the supply may be full-surface supply in which the acid treatment agent is supplied to the entire recording medium or partial supply in which the acid treatment agent is partially supplied to regions in which the ink is supplied in the ink-supplying step. In the present invention, from the viewpoint of uniformly adjusting the amount of a treatment fluid supplied, homogeneously recording fine lines, fine image portions, or the like, and suppressing the density variation such as image variation, the full-surface supply in which the acid treatment agent is supplied to the entire coated paper through coating in which a coating roller or the like is used is preferred.

Examples of a method for applying the acid treatment agent by controlling the amount of the acid treatment agent supplied within the above-described range include a method in which an anilox roller is used. The anilox roller refers to a roller provided with pyramid shapes, diagonal lines, tortoiseshell shapes, or other shapes by processing the surface of a roller on which ceramic has been sprayed using a laser. The treatment fluid permeates into recess portions provided on the roller surface, and is transferred to a paper surface when coming into contact with the paper surface, thereby applying a controlled coating amount in the recesses of the anilox roller.

—Ink-supplying Step—

In the ink-supplying step, the ink composition included in the ink set is supplied onto the recording medium. There is no particular limitation regarding the method for supplying the ink composition as long as the ink composition can be supplied in a desired image pattern, and a well-known ink-supplying method can be used. For example, the ink composition can be supplied onto the recording medium using means of the ink jet method, a mimeographing method, a stamping method, or the like. Among them, from the viewpoint of compacting a recording apparatus and high-speed recording properties, a step of supplying the ink composition using the ink jet method is preferred.

In the formation of an image using the ink jet method, the ink composition is discharged onto the recording medium by donating energy, and a colored image is formed. Meanwhile, as a preferable ink jet recording method for the present invention, the method described in paragraphs 0093 to 0105 in JP2003-306623A can be applied.

The ink jet method is not particularly limited, and may be a well-known method, for example, any of a charge control method in which ink is discharged using an electrostatic attracting force, a drop-on-demand method (a pressure pulse method) in which a vibration pressure of a piezo element is used, an acoustic ink jet method in which ink is discharged using an acoustic beam (radiation pressure) converted from an electric signal, and the like.

In addition, an ink jet head used in the ink jet method may be any of an on-demand method and a continuous method. Furthermore, an ink nozzle and the like used when recording is carried out using the ink jet method are not particularly limited, and can be appropriately selected depending on purpose.

The scope of the ink jet method includes a method in which a number of small volumes of ink having a low concentration called photo ink are sprayed, a method in which image qualities are improved using a plurality of inks having substantially the same hue and different concentrations, and a method in which colorless and transparent ink is used.

As the ink jet method, there are a shuttle method in which recording is carried out using a short serial head (short head) while the serial head is scanned in the width direction of a recording medium and a line method in which a line head in which recording elements are arrayed fully corresponding to one side of a recording medium is used. In the line method, an image can be recorded on the entire surface of a recording medium by scanning the recording medium in a direction orthogonal to the array direction of the recording elements, and a transportation system such as a carriage that scans the short head becomes unnecessary. In addition, the movement of the carriage and the complicated scanning control with a recording medium become unnecessary, and only the recording medium is moved, and therefore the recording speed can be increased compared with the shuttle method.

In the present invention, there is no particular limitation regarding the order of the acid treatment step and the ink-supplying step; however, from the viewpoint of image quality, it is preferable to carry out the ink-supplying step after the acid treatment step. That is, the ink-supplying step is preferably a step of supplying the ink composition onto the recording medium onto which the acid treatment agent has been supplied.

—Photopolymerization Step—

In the formation of an image, a step of radiating light (an active energy ray) on the ink composition supplied onto the recording medium is preferably included. When an active energy ray is radiated, the polymerizing compound included in the ink composition is polymerized, and a cured film including the colorant is formed. As a result, the scratch resistance and blocking resistance of an image are more effectively improved.

The ink composition supplied onto the recording medium is cured when being irradiated with an active energy ray. This is because the photopolymerization initiator included in the ink composition is decomposed by the radiation of the active energy ray, a radical is generated, and the polymerization reaction of the polymerizing compound is initiated and accelerated by the generated radical, whereby the ink composition is cured.

In a case in which an acid is included in the treatment fluid, the ink composition is further aggregated (immobilized) by the acid supplied from the compound when the active energy ray is radiated, and the qualities of an image section (scratch resistance, blocking resistance, and the like) improve.

In the present invention, as the active energy ray, an α ray, a γ ray, an electron beam, an X ray, an ultraviolet ray, a visible ray, an infrared ray, and the like can be used. The photopolymerization initiator used in the present invention strongly absorbs, particularly, light in the ultraviolet range, and therefore the wavelength of the active energy ray is preferably in a range of 200 nm to 600 nm, more preferably in a range of 300 nm to 450 nm, and still more preferably in a range of 350 nm to 420 nm.

The output of the active energy ray is preferably 5000 $mJ/cm^2$ or less, more preferably in a range of 10 $mJ/cm^2$ to 4000 $mJ/cm^2$, and still more preferably in a range of 20 $mJ/cm^2$ to 3000 $mJ/cm^2$.

As an active energy ray source, a mercury lamp, a gas or solid laser, and the like are mainly used, and, as a light source used for the curing of ink for ultraviolet photo-curing ink jet recording, a mercury lamp or a metal halide lamp is widely known. However, currently, there is a strong demand for the removal of mercury from the viewpoint of environmental protection, and the substitution into a GaN-based semiconductor ultraviolet light-emitting device is extremely useful in terms of industrial and environmental senses. In addition, an LED and an LD are small and inexpensive, and have performance of a long service life and high efficiency, and therefore they are expected as light sources for photo-curing ink jet.

In the present invention, a light emitting diode (LED) and a laser diode (LD) can be used as the active energy ray source. Particularly, an ultraviolet LED (UV-LED) and an ultraviolet LD (UV-LD) can be used as an ultraviolet ray source. For example, Nichia Corporation is selling a purple LED in which the main emission spectrum has a wavelength between 365 nm and 420 nm.

A particularly preferable active energy ray source in the present invention is a UV-LED, and a UV-LED having a peak wavelength in a range of 350 nm to 420 nm is preferred.

[Ink-drying Step]

The image-forming method of the present invention may include, if necessary, an ink-drying step in which the solvent (for example, water, the above-described aqueous medium, or the like) in the ink composition supplied onto the recording medium is dried and removed. The ink-drying step is not particularly limited as long as at least a part of the ink solvent can be removed, and it is possible to apply a generally-used method.

EXAMPLES

Hereinafter, the present invention will be described in more detail on the basis of examples, but the present invention is not limited to these examples.

[Preparation of the Polymerizing Compound]

[Chem. 24]

POLYMERIZING COMPOUND

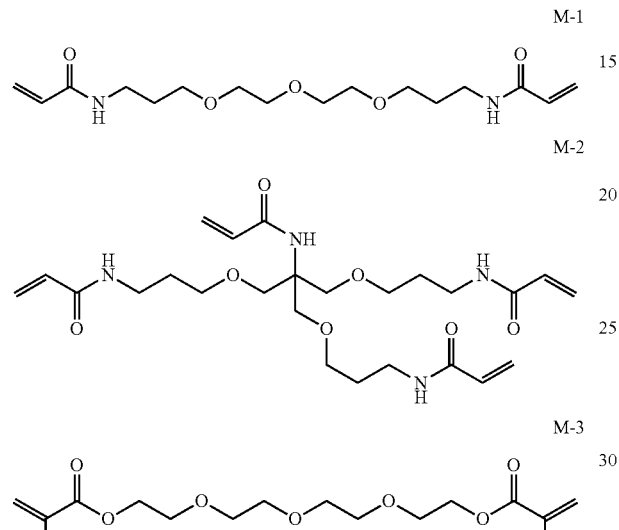

[Synthesis of Polymerizing Compound M-1]

40.0 g (182 mmol) of 4,7,10-trioxa-1,13-tridecanediamine, 37.8 g (450 mmol) of sodium hydrogen carbonate, 100 g of water, and 200 g of tetrahydrofuran were added to a 1 L three neck flask including a stirrer, and 35.2 g (389 mmol) of acrylic acid chloride was added dropwise to the mixture over 20 minutes in an ice bath. The solution after the dropwise addition was stirred at room temperature for five hours, and then tetrahydrofuran was distilled away from the obtained reaction mixture at reduced pressure. Next, a water layer was extracted four times using 200 ml of ethyl acetate, the obtained organic layer was dried using magnesium sulfate, and then was filtered, and a solvent was distilled away at reduced pressure, thereby obtaining 35.0 g (107 mmol, yield 59%) of target solid Polymerizing Compound M-1.

[Synthesis of Polymerizing Compound M-2]

Polymerizing Compound M-2 was synthesized according to the following scheme.

Scheme 2

[Chem. 25]

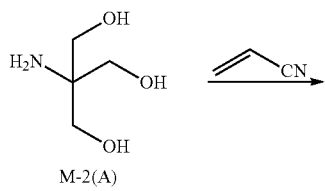

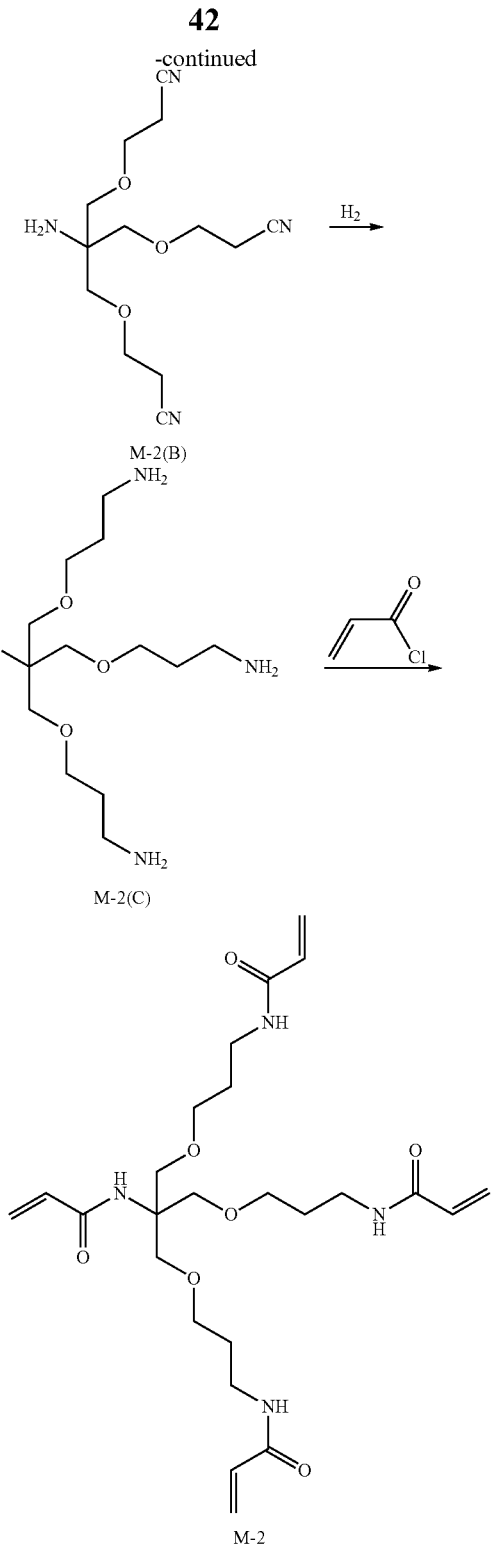

(1) Synthesis of Intermediate M-2 (B)

121 g (1 equivalent) of tris(hydroxymethyl)aminomethane M-2 (A) (manufactured by Tokyo Chemical Industry Co., Ltd.), 84 ml of an aqueous solution of 50% potassium hydroxide, and 423 ml of toluene were added to a 1 L three neck flask including a stirrer bar, and were stirred, and 397.5 g (7.5 equivalents) of acrylonitrile was added dropwise to the mixture over two hours in an ice bath while the reaction system was maintained at 20° C. to 25° C. The solution after the dropwise addition was stirred for 1.5 hours, then, 540 ml of toluene was added to the reaction system, and the reaction mixture was moved into a separating funnel, thereby removing a water layer. After the remaining organic layer was dried using magnesium sulfate, Celite filtration was carried out, and a solvent was distilled away at reduced pressure, thereby obtaining Intermediate M-2 (B): acrylonitrile adduct. The analysis results of the obtained substance using $^1$H-NMR and MS indicated that the substance closely matched a known substance, and thus the substance was used for the subsequent reduction reaction with no additional purification.

(2) Synthesis of Intermediate M-2 (C)

24 g of the previously obtained Intermediate M-2 (B), 48 g of a Ni catalyst (Raney nickel 2400, manufactured by W. R. Grace & Co.), and 600 ml of a solution of 25% ammonia water and methanol (1:1) were put into a 1 L autoclave, were suspended, and the autoclave was sealed. 10 MPa of hydrogen was introduced into the autoclave, and the components were reacted at a reaction temperature of 25° C. for 16 hours.

The disappearance of the raw materials was confirmed through $^1$H-NMR, the reaction mixture was Celite-filtrated, and Celite was washed using methanol several times. A solvent was distilled away from a filtrate at reduced pressure, thereby obtaining Intermediate M-2 (C): amine body. The obtained substance was used for the subsequent reduction reaction with no additional purification.

(3) Synthesis of Polymerizing Compound M-2

30 g of the previously obtained Intermediate M-2 (C), 120 g (14 equivalents) of NaHCO$_3$, 1 L of dichloromethane, and 50 ml of water were added to a 2 L three neck flask including a stirrer. 92.8 g (10 equivalents) of acrylic acid chloride was added dropwise to the mixture over three hours in an ice bath, and then was stirred for three hours at room temperature. The disappearance of the raw materials was confirmed through $^1$H-NMR, then, a solvent was distilled away from the reaction mixture at reduced pressure, the reaction mixture was dried using magnesium sulfate, Celite filtration was carried out, the reaction mixture was washed by applying 100 mL of dichloromethane, and a solvent was distilled away from the filtrate at reduced pressure. Finally, the reaction mixture was purified through column chromatography (ethyl acetate/methanol=4: 1), thereby obtaining a yellow liquid (yield 40%) at normal temperature.

[Polymerizing Compound M-3]

A polymerizing compound manufactured by Tokyo Chemical Industry Co., Ltd. was used as Polymerizing Compound M-3.

[Preparation of a Photopolymerization Initiator]

A photopolymerization initiator manufactured by Tokyo Chemical Industry Co., Ltd. was used as Photopolymerization initiator I-1. Photopolymerization Initiators 1-2 and 1-18 were synthesized with reference to a well-known method (J. Am. Chem. Soc., 2009, 131, 4227).

[Chem. 26]

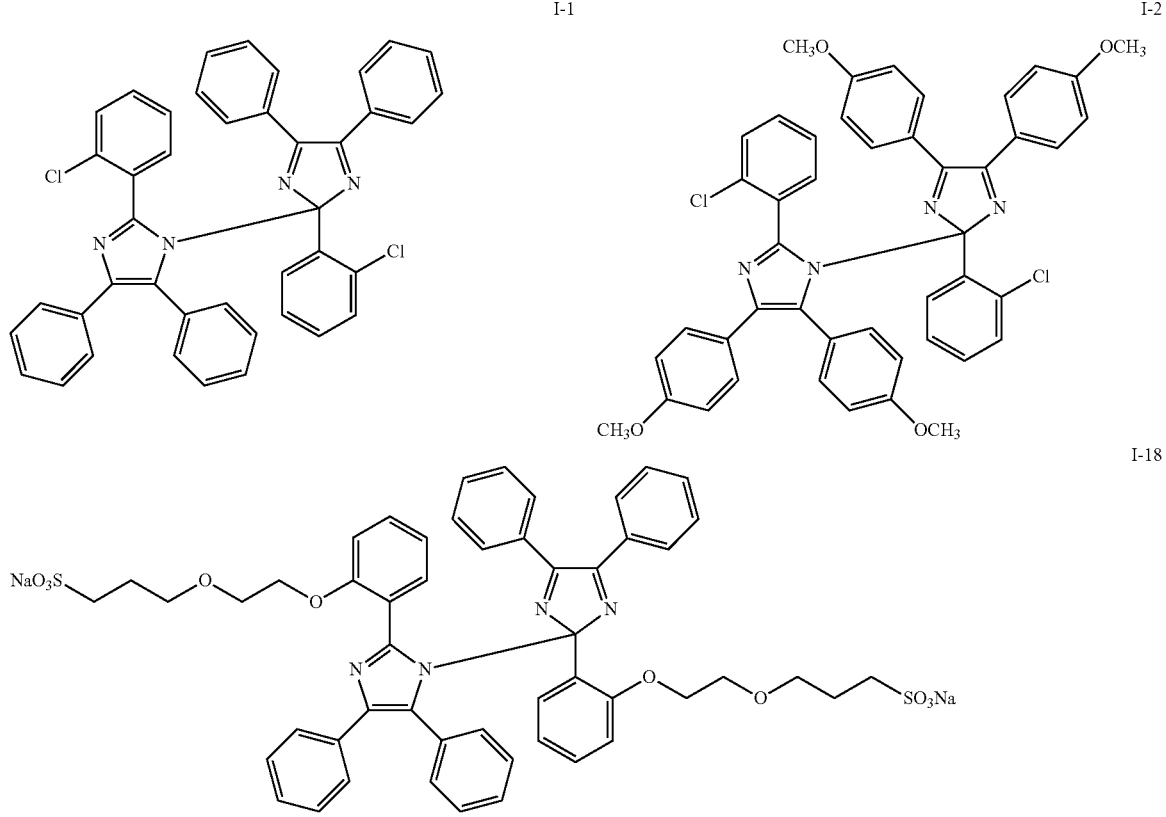

[Hydrogen Donor]

Hydrogen donors manufactured by Tokyo Chemical Industry Co., Ltd. were used as Hydrogen Donors A-1 to A-4 and B-1 to B-3. A compound synthesized according to U.S. Pat. No. 4,520,196A was used as Hydrogen Donor B-4. A compound manufactured by Sigma-Aldrich Co. LLC. was used as Hydrogen Donor B-5. Hydrogen Donor B-6 was synthesized by reacting Hydrogen Donor B-3 with the same moles of potassium hydroxide in water.

[Chem. 27]

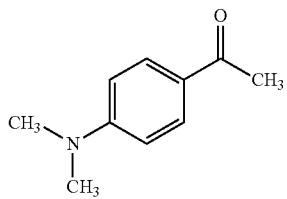
A-1

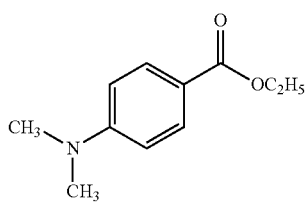
A-2

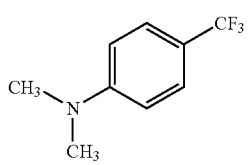
A-3

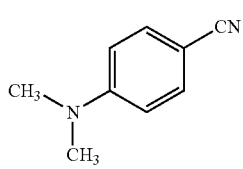
A-4

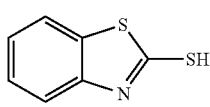
B-1

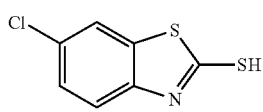
B-2

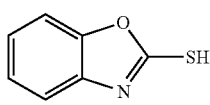
B-3

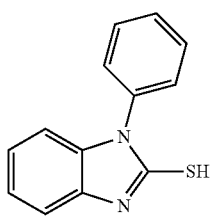
B-4

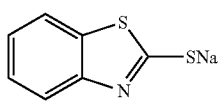
B-5

-continued

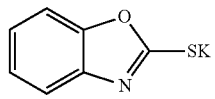
B-6

Regarding the Hammett σp values of individual substituents included in Hydrogen Donors A-1 to A-4 and Hydrogen Donor B-2, the σp of —C(=O)CH$_3$ was 0.50, the σp of C(=O)OC$_2$H$_5$ was 0.45, the σp of —CF$_3$ was 0.54, the σp of —CN was 0.66, and the σp of Cl was 0.23.

Example 1

Individual monomer solutions were prepared in the following manner.

[Preparation of the Monomer Solutions]
(Monomer Solution 1)

Polymerizing Compound M-1 (500 mg), Photopolymerization Initiator I-1 (25 mg), Hydrogen Donor A-1 (25 mg), and malonic acid (50 mg) were dissolved in acetone (2 ml), thereby preparing Monomer Solution 1.

(Monomer Solutions 2 to 10)

Monomer Solutions 2 to 10 were prepared in the same manner as the preparation of Monomer Solution 1 except for the fact that, in the preparation of Monomer Solution 1, Hydrogen Donor A-1 was respectively changed to the same mass of Hydrogen Donors A-2 to A-4 and the same mass of Hydrogen Donors B-1 to B-6.

(Monomer Solutions 11 to 14)

Monomer Solutions 11 to 14 were prepared in the same manner as the preparation of Monomer Solution 2 except for the fact that, in the preparation of Monomer Solution 2, malonic acid was respectively changed to the same mass of benzoic acid, malic acid, phosphoric acid, and acetic acid.

(Monomer Solutions 15 to 18)

Monomer Solutions 15 to 18 were prepared in the same manner as the preparation of Monomer Solution 4 except for the fact that, in the preparation of Monomer Solution 4, malonic acid was respectively changed to the same mass of benzoic acid, malic acid, phosphoric acid, and acetic acid.

(Monomer Solution 19)

Monomer Solution 19 was prepared in the same manner as the preparation of Monomer Solution 2 except for the fact that, in the preparation of Monomer Solution 2, Photopolymerization Initiator I-1 was changed to the same mass of Photopolymerization Initiator I-2.

(Monomer Solutions 20 and 21)

Monomer Solutions 20 and 21 were prepared in the same manner as the preparation of Monomer Solution 15 except for the fact that, in the preparation of Monomer Solution 15, malonic acid was respectively changed to the same mass of malic acid and phosphoric acid.

(Monomer Solution 22)

Monomer Solution 22 was prepared in the same manner as the preparation of Monomer Solution 4 except for the fact that, in the preparation of Monomer Solution 4, Photopolymerization Initiator I-1 was changed to the same mass of Photopolymerization Initiator I-2.

(Monomer Solutions 23 and 24)

Monomer Solutions 23 and 24 were prepared in the same manner as the preparation of Monomer Solution 22 except for the fact that, in the preparation of Monomer Solution 22, malonic acid was respectively changed to the same mass of malic acid and phosphoric acid.

(Monomer Solutions 25 and 26)

Monomer Solutions 25 and 26 were prepared in the same manner as the preparation of Monomer Solution 1 except for the fact that, in the preparation of Monomer Solution 1, Polymerizing Compound M-1 was respectively changed to the same mass of Polymerizing Compounds M-2 and M-3.

[Comparative Hydrogen Donor]

As a comparative subject, Hydrogen Donors R-1 to R-4 (manufactured by Wako Pure Chemical Industries, Ltd.) described below were used.

[Chem. 28]

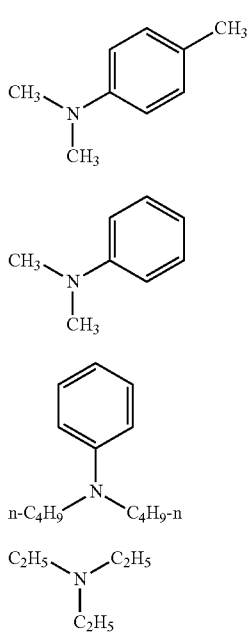

(Monomer Solutions c1 to c4)

Monomer Solutions c1 to c4 were prepared in the same manner as the preparation of Monomer Solution 1 except for the fact that, in the preparation of Monomer Solution 1, Hydrogen Donor A-1 was respectively changed to the same mass of Hydrogen Donors R-1 to R-4.

(Monomer Solution c5)

Monomer Solution c5 was prepared in the same manner as the preparation of Monomer Solution c1 except for the fact that, in the preparation of Monomer Solution c1, Photopolymerization Initiator I-1 was changed to the same mass of Photopolymerization Initiator I-2.

(Monomer Solution c6)

Monomer Solution c6 was prepared in the same manner as the preparation of Monomer Solution c1 except for the fact that, in the preparation of Monomer Solution c1, Hydrogen Donor R-1 was not added.

(Monomer Solutions c7 and c8)

Monomer Solutions c7 and c8 were prepared in the same manner as the preparation of Monomer Solution 1 except for the fact that, in the preparation of Monomer Solution 1, Photopolymerization Initiator I-1 was changed to the same mass of Photopolymerization Initiators J-1 and J-2 described below.

[Chem. 29]

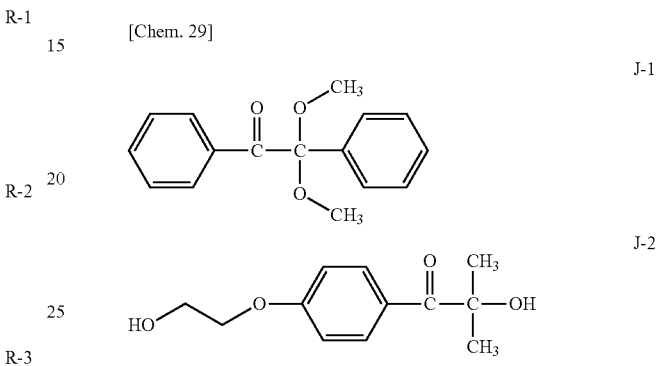

Here, the pKas (in $H_2O$, 25° C.) of the above-described acids are as described below.

Malonic acid: 2.8 (pKa1)
Malic acid: 3.4 (pKa1)
Benzoic acid: 4.2
Phosphoric acid: 2.2 (pKa1)

[Photo-curing Test]

(Test 1)

Monomer Solution 1 (10 μL) was dropped on a copper thin film using a microsyringe, and was exposed for five seconds using an ultraviolet light emitting diode radiation apparatus (365 nm, 110 mW/cm$^2$) manufactured by Nichia Corporation. The degree of a decrease in the peak derived from an unsaturated bond before and after the exposure was observed using an FT-IR (manufactured by Varian Medical Systems, Inc., Varian 3100 FT-IR), and the polymerization ratio was obtained.

(Tests 2 to 26 and c1 to c8)

Tests 2 to 26 and Tests c1 to c8 were carried out in the same manner as Test 1 except for the fact that, in Test 1, Monomer Solution 1 was respectively changed to Monomer Solutions 2 to 26 and Monomer Solutions c1 to c8.

The obtained results are described in Table 1 described below.

TABLE 1

| Test No. | Monomer solution | Photopolymerization initiator | Hydrogen donor | Polymerizing compound | Acid | Polymerization ratio [%] | Note |
|---|---|---|---|---|---|---|---|
| Test 1 | 1 | I-1 | A-1 | M-1 | Malonic acid | 95 | Present Invention |
| Test 2 | 2 | I-1 | A-2 | M-1 | Malonic acid | 94 | Present Invention |
| Test 3 | 3 | I-1 | A-3 | M-1 | Malonic acid | 93 | Present Invention |
| Test 4 | 4 | I-1 | A-4 | M-1 | Malonic acid | 90 | Present Invention |
| Test 5 | 5 | I-1 | B-1 | M-1 | Malonic acid | 83 | Present Invention |
| Test 6 | 6 | I-1 | B-2 | M-1 | Malonic acid | 80 | Present Invention |
| Test 7 | 7 | I-1 | B-3 | M-1 | Malonic acid | 81 | Present Invention |
| Test 8 | 8 | I-1 | B-4 | M-1 | Malonic acid | 83 | Present Invention |
| Test 9 | 9 | I-1 | B-5 | M-1 | Malonic acid | 80 | Present Invention |
| Test 10 | 10 | I-1 | B-6 | M-1 | Malonic acid | 80 | Present Invention |

TABLE 1-continued

| Test No. | Monomer solution | Photopolymerization initiator | Hydrogen donor | Polymerizing compound | Acid | Polymerization ratio [%] | Note |
|---|---|---|---|---|---|---|---|
| Test 11 | 11 | I-1 | A-2 | M-1 | Benzoic acid | 75 | Present Invention |
| Test 12 | 12 | I-1 | A-2 | M-1 | Malic acid | 97 | Present Invention |
| Test 13 | 13 | I-1 | A-2 | M-1 | Phosphoric acid | 71 | Present Invention |
| Test 14 | 14 | I-1 | A-2 | M-1 | Acetic acid | 84 | Present Invention |
| Test 15 | 15 | I-1 | A-4 | M-1 | Benzoic acid | 55 | Present Invention |
| Test 16 | 16 | I-1 | A-4 | M-1 | Malic acid | 96 | Present Invention |
| Test 17 | 17 | I-1 | A-4 | M-1 | Phosphoric acid | 91 | Present Invention |
| Test 18 | 18 | I-1 | A-4 | M-1 | Acetic acid | 55 | Present Invention |
| Test 19 | 19 | 1-2 | A-2 | M-1 | Malonic acid | 83 | Present Invention |
| Test 20 | 20 | 1-2 | A-2 | M-1 | Malic acid | 97 | Present Invention |
| Test 21 | 21 | 1-2 | A-2 | M-1 | Phosphoric acid | 81 | Present Invention |
| Test 22 | 22 | 1-2 | A-4 | M-1 | Malonic acid | 73 | Present Invention |
| Test 23 | 23 | 1-2 | A-4 | M-1 | Malic acid | 100 | Present Invention |
| Test 24 | 24 | 1-2 | A-4 | M-1 | Phosphoric acid | 86 | Present Invention |
| Test 25 | 25 | I-1 | A-1 | M-2 | Malonic acid | 96 | Present Invention |
| Test 26 | 26 | I-1 | A-1 | M-3 | Malonic acid | 90 | Present Invention |
| Test c1 | c1 | I-1 | R-1 | M-1 | Malonic acid | 17 | Comparative Example |
| Test c2 | c2 | I-1 | R-2 | M-1 | Malonic acid | 36 | Comparative Example |
| Test c3 | c3 | I-1 | R-3 | M-1 | Malonic acid | 4 | Comparative Example |
| Test c4 | c4 | I-1 | R-4 | M-1 | Malonic acid | 0 | Comparative Example |
| Test c5 | c5 | I-2 | R-1 | M-1 | Malonic acid | 6 | Comparative Example |
| Test c6 | c6 | I-1 | None | M-1 | Malonic acid | 3 | Comparative Example |
| Test c7 | c7 | J-1 | A-2 | M-1 | Malonic acid | 37 | Comparative Example |
| Test c8 | c8 | J-2 | A-2 | M-1 | Malonic acid | 12 | Comparative Example |

As is clear from the results in Table 1, it is found that, when the biimidazole photopolymerization initiator regulated in the present invention and the hydrogen donor regulated in the present invention were combined together, the polymerization ratio by the radiation of UV-LED light (365 nm) under acidic conditions was significantly excellent.

Here, all of R-1 to R-3 do not have an electron-withdrawing group in the aromatic ring. From this fact, it is found that an electron-withdrawing group needs to be present in an aromatic amine compound that is used as the hydrogen donor to accelerate the polymerization reaction.

In addition, with an aliphatic amine as R-4, the polymerization acceleration effect was not shown.

In addition, even when a photopolymerization initiator other than the photopolymerization initiator regulated in the present invention was combined with the hydrogen donor regulated in the present invention, an effect that extremely improves the polymerization ratio was not obtained.

Example 2

Individual monomer solutions were prepared in the following manner.

[Preparation of the Monomer Solutions]

(Monomer Solution 1A)

Polymerizing Compound M-1 (500 mg), Photopolymerization Initiator I-1 (25 mg), Hydrogen Donor A-1 (25 mg), N-methyl diethanolamine (25 mg), and malonic acid (50 mg) were dissolved in acetone (2 ml), thereby preparing Monomer Solution 1A.

(Monomer Solution 2A)

Monomer Solution 2A was prepared in the same manner as the preparation of Monomer Solution 1A except for the fact that, in the preparation of Monomer Solution 1A, Hydrogen Donor A-1 was changed to the same mass of Hydrogen Donor B-1.

(Monomer Solutions 3A and 4A)

Monomer Solutions 3A and 4A were prepared in the same manner as the preparation of Monomer Solution 2A except for the fact that, in the preparation of Monomer Solution 2A, N-methyl diethanolamine was respectively changed to the same mass of triethylamine and triisopropanolamine.

(Monomer Solutions 5A to 7A)

Monomer Solutions 5A to 7A were prepared in the same manner as the preparation of Monomer Solution 1A except for the fact that, in the preparation of Monomer Solution 1A, Hydrogen Donor A-1 was respectively changed to the same mass of Hydrogen Donors B-2 to B-4.

(Monomer Solutions 8A to 11A)

Monomer Solutions 8A to 11A were prepared in the same manner as the preparation of Monomer Solution 2A except for the fact that, in the preparation of Monomer Solution 2A, malonic acid was respectively changed to the same mass of benzoic acid, malic acid, phosphoric acid, and acetic acid.

(Monomer Solution 12A)

Monomer Solution 12A was prepared in the same manner as the preparation of Monomer Solution 2A except for the fact that, in the preparation of Monomer Solution 2A, Photopolymerization Initiator I-1 was changed to the same mass of Photopolymerization Initiator I-2.

(Monomer Solution 13A)

Monomer Solution 13A was prepared in the same manner as the preparation of Monomer Solution 2A except for the fact that, in the preparation of Monomer Solution 2A, Photopolymerization Initiator I-1 was changed to the same mass of Photopolymerization Initiator I-18, and the solvent was changed from acetone to the same mass of methanol.

(Monomer Solutions 14A and 15A)

Monomer Solutions 14A and 15A were prepared in the same manner as the preparation of Monomer Solution 2A except for the fact that, in the preparation of Monomer Solution 2A, Polymerizing Compound M-1 was respectively changed to the same mass of Polymerizing Compounds M-2 and M-3.

(Monomer Solution c1A)

Monomer Solution c1A was prepared in the same manner as the preparation of Monomer Solution 2A except for the fact that, in the preparation of Monomer Solution 2A, malonic acid was not added.

(Monomer Solution c2A)

Monomer Solution c2A was prepared in the same manner as the preparation of Monomer Solution 2A except for the fact that, in the preparation of Monomer Solution 2A, Hydrogen Donor B-1 was not added.

[Photo-curing Test]

(Test 1A)

Monomer Solution 1A (10 μL) was dropped on a copper thin film using a microsyringe, and was exposed for two seconds using an ultraviolet light emitting diode radiation apparatus (365 nm, 270 mW/cm$^2$) manufactured by Nichia Corporation. The degree of a decrease in the peak derived from an unsaturated bond before and after the exposure was observed using an FT-IR (manufactured by Varian Medical Systems, Inc., Varian 3100 FT-IR), and the polymerization ratio was obtained.

(Tests 2A to 15A and c1A to c2A)

Tests 2A to 15A and c1A to c2A were carried out in the same manner as Test 1A except for the fact that, in Test 1A, Monomer Solution 1A was respectively changed to Monomer Solutions 2A to 15A and Monomer Solutions c1A to c2A.

The obtained results are described in Table 2 described below.

LED light (365 nm) further improved. In addition, it is found from the result of Test c1A that acidic conditions are required for an efficient polymerization reaction.

Example 3

(Monomer Solutions 101 to 118)

Monomer Solutions 101 to 118 were prepared in the same manner as the preparation of Monomer Solution 1 except for the fact that, in Monomer Solutions 1 to 4 and 11 to 24 in Example 1, the acid was not added.

[Photo-curing Test]

(Test 1B)

A photo-curing test was carried out in the same manner as Test 1 in Example 1 using Monomer Solution 101 (10 μL). The polymerization ratio obtained in Example 1 in which the acid was present was subtracted by the polymerization ratio of the monomer solution in which the corresponding acid was not present, thereby obtaining a Δ polymerization ratio (%).

(Tests 2B to 20B)

Tests 2B to 18B were carried out in the same manner as Test 1B except for the fact that, in Test 1B, Monomer Solution 101 was changed to Monomer Solutions 102 to 118.

TABLE 2

| Test No. | Monomer solution | Photopolymerization initiator | Hydrogen donor | Polymerizing compound | Acid | Trialkylamine | Polymerization ratio [%] | Note |
|---|---|---|---|---|---|---|---|---|
| Test 1A | 1A | I-1 | A-1 | M-1 | Malonic acid | N-methyl diethanolamine | 98 | Present Invention |
| Test 2A | 2A | I-1 | B-1 | M-1 | Malonic acid | N-methyl diethanolamine | 95 | Present Invention |
| Test 3A | 3A | I-1 | B-1 | M-1 | Malonic acid | Triethylamine | 93 | Present Invention |
| Test 4A | 4A | I-1 | B-1 | M-1 | Malonic acid | Triisopropanolamine | 95 | Present Invention |
| Test 5A | 5A | I-1 | B-2 | M-1 | Malonic acid | N-methyl diethanolamine | 93 | Present Invention |
| Test 6A | 6A | I-1 | B-3 | M-1 | Malonic acid | N-methyl diethanolamine | 90 | Present Invention |
| Test 7A | 7A | I-1 | B-4 | M-1 | Malonic acid | N-methyl diethanolamine | 93 | Present Invention |
| Test 8A | 8A | I-1 | B-1 | M-1 | Benzoic acid | N-methyl diethanolamine | 91 | Present Invention |
| Test 9A | 9A | I-1 | B-1 | M-1 | Malic acid | N-methyl diethanolamine | 95 | Present Invention |
| Test 10A | 10A | I-1 | B-1 | M-1 | Phosphoric acid | N-methyl diethanolamine | 89 | Present Invention |
| Test 11A | 11A | I-1 | B-1 | M-1 | Acetic acid | N-methyl diethanolamine | 93 | Present Invention |
| Test 12A | 12A | I-2 | B-1 | M-1 | Malonic acid | N-methyl diethanolamine | 95 | Present Invention |
| Test 13A | 13A | I-18 | B-1 | M-1 | Malonic acid | N-methyl diethanolamine | 80 | Present Invention |
| Test 14A | 14A | I-1 | B-1 | M-2 | Malonic acid | N-methyl diethanolamine | 91 | Present Invention |
| Test 15A | 15A | I-1 | B-1 | M-3 | Malonic acid | N-methyl diethanolamine | 93 | Present Invention |
| Test c1A | c1A | I-1 | B-1 | M-1 | None | N-methyl diethanolamine | 0 | Comparative Example |
| Test c2A | c2A | I-1 | None | M-1 | Malonic acid | N-methyl diethanolamine | 0 | Comparative Example |

As is clear from the comparison between the results in Table 1 and the results in Table 2, it is found that, when trialkylamine was present, the polymerization ratio with UV- The obtained results are described in Table 3 described below.

TABLE 3

| Test No. | Photopolymerization initiator | Hydrogen donor | Polymerizing compound | Acid | Δ polymerization ratio [%] | Solvent in monomer solution | Note |
|---|---|---|---|---|---|---|---|
| Test 1B | I-1 | A-1 | M-1 | Malonic acid | 93 | Acetone | Present Invention |

TABLE 3-continued

| Test No. | Photopolymerization initiator | Hydrogen donor | Polymerizing compound | Acid | Δ polymerization ratio [%] | Solvent in monomer solution | Note |
|---|---|---|---|---|---|---|---|
| Test 2B | I-1 | A-2 | M-1 | Malonic acid | 93 | Acetone | Present Invention |
| Test 3B | I-1 | A-3 | M-1 | Malonic acid | 93 | Acetone | Present Invention |
| Test 4B | I-1 | A-4 | M-1 | Malonic acid | 90 | Acetone | Present Invention |
| Test 5B | I-1 | A-2 | M-1 | Benzoic acid | 74 | Acetone | Present Invention |
| Test 6B | I-1 | A-2 | M-1 | Malic acid | 96 | Acetone | Present Invention |
| Test 7B | I-1 | A-2 | M-1 | Phosphoric acid | 70 | Acetone | Present Invention |
| Test 8B | I-1 | A-2 | M-1 | Acetic acid | 83 | Acetone | Present Invention |
| Test 9B | I-1 | A-4 | M-1 | Benzoic acid | 55 | Acetone | Present Invention |
| Test 10B | I-1 | A-4 | M-1 | Malic acid | 96 | Acetone | Present Invention |
| Test 11B | I-1 | A-4 | M-1 | Phosphoric acid | 91 | Acetone | Present Invention |
| Test 12B | I-1 | A-4 | M-1 | Acetic acid | 55 | Acetone | Present Invention |
| Test 13B | I-2 | A-2 | M-1 | Malonic acid | 82 | Acetone | Present Invention |
| Test 14B | I-2 | A-2 | M-1 | Malic acid | 96 | Acetone | Present Invention |
| Test 15B | I-2 | A-2 | M-1 | Phosphoric acid | 80 | Acetone | Present Invention |
| Test 16B | I-2 | A-4 | M-1 | Malonic acid | 72 | Acetone | Present Invention |
| Test 17B | I-2 | A-4 | M-1 | Malic acid | 98 | Acetone | Present Invention |
| Test 18B | I-2 | A-4 | M-1 | Phosphoric acid | 83 | Acetone | Present Invention |

As is clear from Table 3, it is found that the polymerization ratio of the monomer solution in a case in which the hydrogen donor of the present invention was used significantly improved under acidic conditions.

Example 4

Individual monomer solutions were prepared in the following manner.
[Preparation of the Monomer Solutions]
(Monomer Solution 201)
Polymerizing Compound M-1 (200 mg), Photopolymerization Initiator I-1 (10 mg), Hydrogen Donor B-1 (10 mg), and malonic acid (20 mg) were dissolved in acetonitrile (8 ml)/pure water (2 ml), thereby preparing Monomer Solution 201.
(Monomer Solutions 202 and 203)
Monomer Solutions 202 and 203 were prepared in the same manner as the preparation of Monomer Solution 1 except for the fact that, in the preparation of Monomer Solution 201, Hydrogen Donor B-1 was respectively changed to the same mass of Hydrogen Donors B-2 and B-3.
(Monomer Solutions 204 and 205)
Monomer Solution 204 was prepared in the same manner as the preparation of Monomer Solution 201 except for the fact that, in the preparation of Monomer Solution 201, malonic acid was changed to the same mass of malic acid.
Monomer Solution 205 was prepared in the same manner as the preparation of Monomer Solution 202 except for the fact that, in the preparation of Monomer Solution 202, malonic acid was changed to the same mass of malic acid.
(Monomer Solution 206)
Monomer Solution 206 was prepared by, before exposure, bubbling Monomer Solution 201 for three minutes using argon gas, and substituting air in a UV-Vis quartz cell by argon gas.
(Monomer Solutions c21 to c23)
Monomer Solutions c21 to c23 were prepared in the same manner as the preparation of Monomer Solutions 201 to 203 except for the fact that, in the preparation of Monomer Solutions 201 to 203, malonic acid was not added respectively.
(Monomer Solutions c24 to c27)
Monomer Solutions c24 to c27 were prepared in the same manner as the preparation of Monomer Solution 1 except for the fact that, in the preparation of Monomer Solution 201, Hydrogen Donor B-1 was respectively changed to Hydrogen Donors R-1 to R-4.
(Monomer Solution c28)
Monomer Solution c28 was prepared by, before exposure, bubbling Monomer Solution c24 for three minutes using argon gas, and substituting air in a UV-Vis quartz cell by argon gas.
(Monomer Solution c29)
Monomer Solution c29 was prepared in the same manner as the preparation of Monomer Solution 201 except for the fact that, in the preparation of Monomer Solution 201, Hydrogen Donor B-1 was not added.
[Photo-curing Test]
(Test 1C)
Monomer Solution 201 (1.5 mL) was put into a UV-Vis quartz cell, the cell was sealed using a lid, and the monomer solution was exposed for 20 seconds using the ultraviolet light emitting diode radiation apparatus used in Example 1. The polymerization ratio was obtained from a decrease in Polymerizing Compound M-1 before and after the exposure using HPLC.
(Tests 2C to 6C and c1C to c9C)
Tests 2C to 6C and Tests c1C to c9C were carried out in the same manner as Test 1C except for the fact that, in Test 1C, Monomer Solution 201 was respectively changed to Monomer Solutions 202 to 206 and Monomer Solutions c21 to c29.
The obtained results are described in Table 4 described below.
Meanwhile, AR in the "solvent in monomer solution" column in the table represents acetonitrile.

TABLE 4

| Test No. | Photopolymerization initiator | Hydrogen donor | Polymerizing compound | Acid | Ar gas substitution | Δ polymerization ratio [%] | Solvent in monomer solution | Note |
|---|---|---|---|---|---|---|---|---|
| Test 1C | I-1 | B-1 | M-1 | Malonic acid | No | 30 | AR/H$_2$0 | Present Invention |
| Test 2C | I-1 | B-2 | M-1 | Malonic acid | No | 33 | AR/H$_2$0 | Present Invention |

TABLE 4-continued

| Test No. | Photopolymerization initiator | Hydrogen donor | Polymerizing compound | Acid | Ar gas substitution | Δ polymerization ratio [%] | Solvent in monomer solution | Note |
|---|---|---|---|---|---|---|---|---|
| Test 3C | I-1 | B-3 | M-1 | Malonic acid | No | 30 | AR/H$_2$0 | Present Invention |
| Test 4C | I-1 | B-1 | M-1 | Malic acid | No | 32 | AR/H$_2$0 | Present Invention |
| Test 5C | I-1 | B-2 | M-1 | Malic acid | No | 33 | AR/H$_2$0 | Present Invention |
| Test 6C | I-1 | B-1 | M-1 | Malonic acid | Yes | 51 | AR/H$_2$0 | Present Invention |
| Test c1C | I-1 | B-1 | M-1 | None | No | 5 | AR/H$_2$0 | Comparative Example |
| Test c2C | I-1 | B-2 | M-1 | None | No | 5 | AR/H$_2$0 | Comparative Example |
| Test c3C | I-1 | B-3 | M-1 | None | No | 3 | AR/H$_2$0 | Comparative Example |
| Test c4C | I-1 | R-1 | M-1 | Malonic acid | No | 2 | AR/H$_2$0 | Comparative Example |
| Test c5C | I-1 | R-2 | M-1 | Malonic acid | No | 1 | AR/H$_2$0 | Comparative Example |
| Test c6C | I-1 | R-3 | M-1 | Malonic acid | No | 0 | AR/H$_2$0 | Comparative Example |
| Test c7C | I-1 | R-4 | M-1 | Malonic acid | No | 0 | AR/H$_2$0 | Comparative Example |
| Test c8C | I-1 | R-1 | M-1 | Malonic acid | Yes | 10 | AR/H$_2$0 | Comparative Example |
| Test c9C | I-1 | None | M-1 | Malonic acid | No | 0 | AR/H$_2$0 | Comparative Example |

As is clear from Table 4, it is found that all of the monomer solutions of the present invention had excellent polymerization ratios.

Example 5

An ink set was produced in the following manner, an image was formed using the ink jet method, and a curing property test was carried out.

[Synthesis of Polymer Dispersing Agent P-1]

88 g of methyl ethyl ketone was added to a 1000 ml three neck flask including a stirrer and a cooling pipe, was heated at 72° C. in a nitrogen atmosphere, and a solution obtained by dissolving 0.85 g of dimethyl 2,2'-azobisisobutyrate, 60 g of benzyl methacrylate, 10 g of methacrylic acid, and 30 g of methyl methacrylate in 50 g of methyl ethyl ketone was added dropwise to the methyl ethyl ketone for three hours. After the dropwise addition, the components were further reacted for one hour, then, a solution obtained by dissolving 0.42 g of dimethyl 2,2'-azobisisobutyrate in 2 g of methyl ethyl ketone was added, and was heated at 78° C. for four hours. The obtained reaction solution was re-precipitated twice in an extremely excessive amount of hexane, and the educed resin was dried, thereby obtaining 96 g of Polymer Dispersing agent P-1.

The composition of the obtained resin was confirmed through $^1$H-NMR, and the mass-average molecular weight (Mw) obtained through gel permeation chromatography (GPC) was 44,600. Furthermore, as a result of obtaining the acid value using the method described in JIS standards (JISK0070:1992), the acid value was 65.2 mgKOH/g.

[Preparation of a Resin-coated Pigment Dispersion]

—Resin-coated Magenta Pigment Dispersion—

10 parts by mass of Chromophthal Jet Magenta DMQ (Pigment Red 122, manufactured by BASF Japan Ltd.), 5 parts by mass of Polymer Dispersing agent P-1, 42 parts by mass of methyl ethyl ketone, 5.5 parts by mass of an aqueous solution of 1 mol/L NaOH, and 87.2 parts by mass of ion exchange water were mixed together, and were dispersed for two hours to six hours using a beads mill in which 0.1 mmϕ zirconia beads were used, thereby obtaining a dispersed substance.

Methyl ethyl ketone was removed from the obtained dispersed substance at reduced pressure at 55° C., and furthermore, some of the water was removed, thereby obtaining a resin-coated magenta pigment dispersion (coloring particles) having a pigment concentration of 40 mass %.

[Preparation of Ink Sets 1 to 4]

Magenta Inks 1 to 4 were prepared on the basis of Ink Formulations 1 to 4 described below. In addition, Acid Treatment Agent 1 was prepared on the basis of Formulation described below. Ink Sets 1 to 4 made of a combination of each of Magenta inks 1 to 4 and Acid Treatment Agent 1 were obtained.

(Preparation of Magenta Inks 1 to 4)

A resin-coated magenta pigment dispersion, ion exchange water, a photopolymerization initiator, a polymerizing compound, and a surfactant were mixed so as to obtain Ink Formulations 1 to 4 described below using the resin-coated magenta pigment dispersion, and then the mixture was filtered using a 5 μm membrane filter, thereby preparing Magenta Inks 1 to 4.

—Ink Formulation 1—

| | |
|---|---|
| Resin-coated magenta pigment dispersion | 15 mass % |
| Photopolymerization Initiator I-1 | 1.5 mass % |
| Hydrogen Donor B-5 | 1.5 mass % |
| Polymerizing Compound M-1 | 15 mass % |
| Olefin E1010 | 1 mass % |
| (manufactured by Nissin Chemical Co., Ltd.; surfactant) | |
| Acetonitrile | 60 mass % |
| Ion exchange water | added so that the total amount reached 100 mass % |

—Ink Formulation 2—

| | |
|---|---|
| Resin-coated magenta pigment dispersion | 15 mass % |
| Photopolymerization Initiator I-2 | 1.5 mass % |
| Hydrogen Donor B-5 | 1.5 mass % |
| Polymerizing Compound M-1 | 15 mass % |
| Olefin E1010 | 1 mass % |
| (manufactured by Nissin Chemical Co., Ltd.; surfactant) | |
| Acetonitrile | 60 mass % |
| Ion exchange water | added so that the total amount reached 100 mass % |

—Ink Formulation 3—

| | |
|---|---|
| Resin-coated magenta pigment dispersion | 15 mass % |
| Photopolymerization Initiator I-1 | 1.5 mass % |
| Hydrogen Donor A-1 | 1.5 mass % |
| Polymerizing Compound M-1 | 15 mass % |
| Olefin E1010 | 1 mass % |
| (manufactured by Nissin Chemical Co., Ltd.; surfactant) | |
| Acetonitrile | 60 mass % |
| Ion exchange water | added so that the total amount reached 100 mass % |

—Ink Formulation 4 (Comparative Ink Formulation)—

| Resin-coated magenta pigment dispersion | 15 mass % |
|---|---|
| Photopolymerization Initiator I-1 | 3 mass % |
| Polymerizing Compound M-1 | 15 mass % |
| Olefin E1010 | 1 mass % |
| (manufactured by Nissin Chemical Co., Ltd.; surfactant) | |
| Acetonitrile | 60 mass % |
| Ion exchange water | added so that the total amount reached 100 mass % |

As a result of measuring the pHs (25° C.) of Magenta Inks 1 to 4 using a pH meter WM-50EG (manufactured by DKK-Toa Corporation), the pH values were all 8.8.

(Preparation of an Acid Treatment Agent)

The following materials were mixed, thereby preparing Acid Treatment Agent 1. As a result of measuring the pH (25° C.) of Acid Treatment Agent 1 using the above-described pH meter, the pH was 1.0.

—Composition of Acid Treatment Agent 1—

| Malonic acid | 25.0 mass % |
|---|---|
| Tripropylene glycol monomethyl ether | 5.0 mass % |
| (water-soluble organic solvent) | |
| Ion exchange water | 70.0 mass % |

[Preparation of Ink Set 5]

Ink Set 5 was produced using only Magenta Ink 1 without combining Acid Treatment Agent 1.

[Ink Jet Recording]

As a recording medium (coated paper), Tokubishi Art Double-sided N (manufactured by Mitsubishi Paper Mills Limited) (basis weight 104.7 g/m$^2$) was prepared, an image was formed as described below, and the formed image was evaluated as described below.

Line images and solid images were formed through four-color single pass recording using Ink Sets 1 to 5 prepared above.

At this time, regarding the line images, line images were formed in forms of a line as wide as one dot of 1200 dpi, a line as wide as two dots, and a line as wide as four dots by discharging the ink compositions in the main scanning direction through a single pass.

In addition, the solid images were formed by discharging the ink compositions to the entire surfaces of recording media (samples) cut into the A5 size. A variety of conditions for forming the images are as described below.

Here, the following (1) and (2) are steps carried out for only Ink Sets 1 to 4.

(1) Acid Treatment Agent-supplying Step

For Ink Sets 1 to 4, Acid Treatment Agent 1 was applied to the entire surfaces of the recording media using a roll coater in which the application amount was controlled using an anilox roller (the number of lines per inch was in a range of 100 to 300) so that the supply amount reached 1.4 g/m$^2$.

(2) Drying Treatment and Permeation Treatment Step

Next, on the recording media to which the acid treatment agent had been applied, a drying treatment and a permeation treatment were carried out under the following conditions.

Wind speed: 10 m/s

Temperature: the recording medium was heated using a contact-type planar heater from the side (rear surface side) opposite to the recording surface side of the recording medium so that the surface temperature of the recording medium on the recording surface side reached 60° C.

(3) Ink-Supplying Step

Ink was discharged using the ink jet method under the following conditions to the surface (recording surface side) of the recording medium on which the acid treatment agent had been applied for Ink Sets 1 to 4, and to the recording surface of the recording medium for Ink Set 5, thereby forming line images and solid images respectively.

Head: as many as four colors of piezo full line heads as wide as 1,200 dpi/20 inch were disposed Amount of liquid droplets discharged: 2.0 pL Driving frequency: 30 kHz (4) Ink-Drying Step The recording media to which the ink had been supplied were dried under the following conditions.

Drying method: blast drying

Wind speed: 15 m/s

Temperature: the recording medium was heated using a contact-type planar heater from the side (rear surface side) opposite to the recording surface side of the recording medium so that the surface temperature of the recording medium on the recording surface side reached 60° C.

(5) Immobilizing Step

Next, an ultraviolet ray was radiated on the recorded images as the active energy ray using a metal halide lamp under an energy condition of 2000 mJ/cm$^2$, thereby obtaining image samples.

[Evaluation]

The obtained respective image samples were subjected to the curing property test of ink, and the curing properties were evaluated as described below.

—Curing Property Test—

Non-printed Tokubishi Art Double-sided N (manufactured by Mitsubishi Paper Mills Limited) was coiled around a paperweight (mass 470 g, size: 15 mm×30 mm×120 mm) (the contact area between the non-printed Tokubishi Art Double-sided N and an evaluation sample was 150 mm$^2$), and the printed sample was rubbed three times (equivalent of a load of 260 kg/m$^2$). The rubbed printed surface was visually observed, and was evaluated according to the following evaluation standards.

(Evaluation Standards)

A . . . The image (color material) on the printed surface was not peeled off.

B . . . The image (color material) on the printed surface was slightly peeled off.

C . . . The image (color material) on the printed surface was peeled off, and a practical problem was caused.

The obtained results are described in Table 5 described below.

TABLE 5

| Ink set | Photopolymerization initiator | Hydrogen donor | Acid treatment agent | Polymerizing compound | Evaluation results of curing properties | Note |
|---|---|---|---|---|---|---|
| 1 | I-1 | B-5 | Yes | M-1 | A | Present Invention |
| 2 | 1-2 | B-5 | Yes | M-1 | A | Present Invention |

TABLE 5-continued

| Ink set | Photopolymerization initiator | Hydrogen donor | Acid treatment agent | Polymerizing compound | Evaluation results of curing properties | Note |
|---|---|---|---|---|---|---|
| 3 | I-1 | A-1 | Yes | M-1 | A | Present Invention |
| 4 | I-1 | None | Yes | M-1 | C | Comparative Example |
| 5 | I-1 | B-5 | No | M-1 | C | Comparative Example |

As is clear from Table 5, the images (the line images and the solid images) formed using the ink set of the present invention were all excellent in terms of curing properties. From this fact, it is found that the ink set of the present invention is suitable for the formation of an image using the ink jet method.

[Preparation of Ink Sets 6 to 8]

Magenta Inks 6 to 8 were prepared on the basis of Ink Formulations 6 to 8 described below. In addition, Acid Treatment Agent 1 described above was used as an acid treatment agent. Ink Sets 6 to 8 made of a combination of each of the magenta inks and Acid Treatment Agent 1 were obtained.

(Preparation of Magenta Inks 6 to 8)

A resin-coated magenta pigment dispersion, ion exchange water, a photopolymerization initiator, a polymerizing compound, and a surfactant were mixed so as to obtain Ink Formulations 6 to 8 described below using the resin-coated magenta pigment dispersion, and then the mixture was filtered using a 5 μm membrane filter, thereby preparing Magenta Inks 6 to 8.

—Ink Formulation 6—

| | |
|---|---|
| Resin-coated magenta pigment dispersion | 15 mass % |
| Photopolymerization Initiator I-18 | 1.5 mass % |
| Hydrogen Donor B-5 | 1.5 mass % |
| N-methyl diethanolamine | 1.5 mass % |
| Polymerizing Compound M-1 | 15 mass % |
| Olefin E1010 (manufactured by Nissin Chemical Co., Ltd.; surfactant) | 1 mass % |
| Ion exchange water | added so that the total amount reached 100 mass % |

—Ink Formulation 7—

| | |
|---|---|
| Resin-coated magenta pigment dispersion | 15 mass % |
| Photopolymerization Initiator I-18 | 1.5 mass % |

-continued

| | |
|---|---|
| Hydrogen Donor B-6 | 1.5 mass % |
| N-methyl diethanolamine | 1.5 mass % |
| Polymerizing Compound M-1 | 15 mass % |
| Olefin E1010 (manufactured by Nissin Chemical Co., Ltd.; surfactant) | 1 mass % |
| Ion exchange water | added so that the total amount reached 100 mass % |

—Ink Formulation 8—

| | |
|---|---|
| Resin-coated magenta pigment dispersion | 15 mass % |
| Photopolymerization Initiator I-18 | 1.5 mass % |
| Hydrogen Donor B-5 | 1.5 mass % |
| Triisopropanolamine | 1.5 mass % |
| Polymerizing Compound M-1 | 15 mass % |
| Olefin E1010 (manufactured by Nissin Chemical Co., Ltd.; surfactant) | 1 mass % |
| Ion exchange water | added so that the total amount reached 100 mass % |

As a result of measuring the pHs (25° C.) of Magenta Inks 6 to 8 using a pH meter WM-50EG (manufactured by DKK-Toa Corporation), the pH values were all 8.8.

[Preparation of Ink Set 9]

Ink Set 9 was produced using only Magenta Ink 6 without combining Acid Treatment Agent 1.

[Ink Jet Recording]

As a recording medium (coated paper), Tokubishi Art Double-sided N (manufactured by Mitsubishi Paper Mills Limited) (basis weight 104.7 g/m$^2$) was prepared, an image was formed as described below, and the formed image was evaluated as described below.

Line images and solid images were formed using the same method as the above-described method for four-color single pass recording (ink jet recording) using Ink Sets 6 to 9 prepared above. Meanwhile, on Ink Set 9, the acid treatment agent-supplying step and the subsequent drying treatment and permeation treatment were not carried out.

[Evaluation]

For the obtained respective image samples, the curing properties were evaluated using the same evaluation method and evaluation standards as described above.

The obtained results are described in Table 6 described below.

TABLE 6

| Ink set | Photopolymerization initiator | Hydrogen donor | Acid treatment agent | Polymerizing compound | Trialkylamine | Evaluation results of curing properties | Note |
|---|---|---|---|---|---|---|---|
| 6 | I-18 | B-5 | Yes | M-1 | N-methyl diethanolamine | A | Present Invention |
| 7 | I-18 | B-6 | Yes | M-1 | N-methyl diethanolamine | A | Present Invention |
| 8 | I-18 | B-5 | Yes | M-1 | Triisopropanolamine | A | Present Invention |
| 9 | I-18 | B-5 | No | M-1 | N-methyl diethanolamine | C | Comparative Example |

As is clear from Table 6, the images (the line images and the solid images) formed using the ink set of the present invention were all excellent in terms of curing properties. From this fact, it is found that the ink set of the present invention is suitable for the formation of an image using the ink jet method.

What is claimed is:
1. An ink set comprising:
an ink composition including

(A) a polymerizing compound having an ethylenic unsaturated group,
(B) a photopolymerization initiator represented by Formula (1) described below, and
(C) a hydrogen donor having a structure in which a nitrogen atom is directly bonded to an aromatic ring, in which the aromatic ring has an electron-withdrawing group or the nnitrogen atom constitutes a hetero ring; and
an acid treatment agent including an acidic compound,
wherein (C) the hydrogen donor is expresses by Formula (2) describe below,

FORMULA (1)

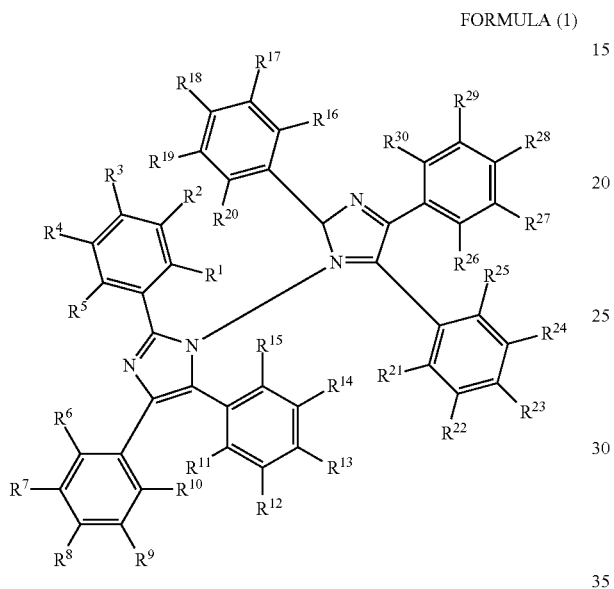

in Formula (1), each of $R^1$ to $R^{30}$ represents a hydrogen atom, a halogen atom, an alkyl group, or an alkoxy group,

FORMULA (2')

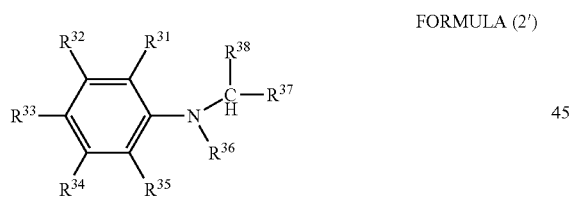

in formula (2), each of $R^{31}$ to $R^{35}$ represents a hydrogen atom or a substituent, here at least one of $R^{31}$ to $R^{35}$ is an electron-withdrawing group, $R^{36}$ represents a hydrogen atom, an alkyl group, or an aryl group, each of $R^{37}$ and $R^{38}$ represents a hydrogen atom or an alkyl group, X represents an oxygen atom, a sulfer atom, or a nitrogen atom having a substituent.

2. The ink set according to claim 1,
wherein the ink composition includes (D) trialkylamine.

3. The ink set according to claim 1,
wherein the acidic compound is an acid having a molecular weight in a range of 50 to 200 and a pKa in water in a range of 1 to 5.

4. The ink set according to claim 1,
wherein (A) the polymerizing compound having an ethylenic unsaturated group is a (meth)acrylate compound having two or more (meth)acryloyl groups or a (meth)acrylamide compound having two or more (meth)acrylamide groups.

5. The ink set according to claim 1,
wherein the ink composition includes (E) a colorant.

6. An ink composition comprising:
(A) a polymerizing compound having an ethylenic unsaturated group;
(B) a photopolymerization initiator represented by Formula (1) described below; and
(C) a hydrogen donor represented by Formula (2') described below,

FORMULA (1)

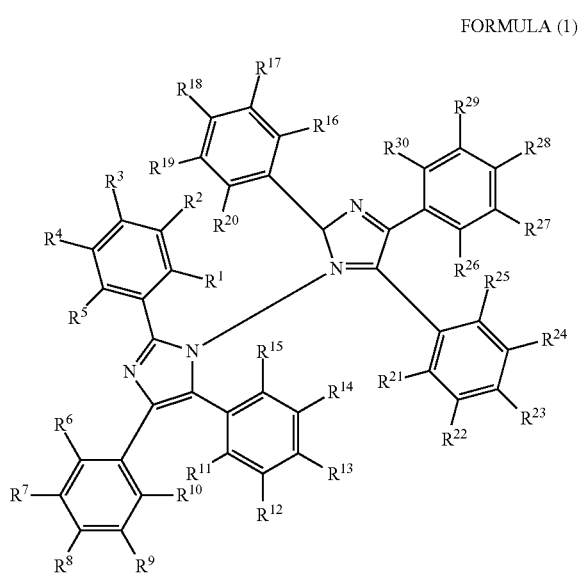

in Formula (1), each of $R^1$ to $R^{30}$ represents a hydrogen atom, a halogen atom, an alkyl group, or an alkoxy group,

FORMULA (2')

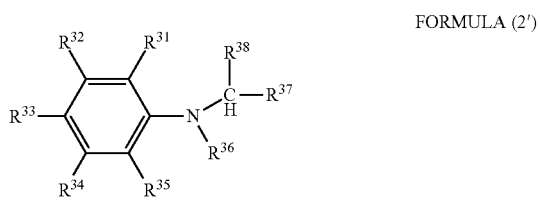

in Formula (2'), each of $R^{31}$ to $R^{35}$ represents a hydrogen atom or a substituent, at least one of $R^{31}$ to $R^{35}$ is an electron-withdrawing group having a positive Hammett σ value,
$R^{36}$ represents a hydrogen atom, an alkyl group, or an aryl group, and
each of $R^{37}$ and $R^{38}$ represents a hydrogen atom or an alkyl group.

7. The ink composition according to claim 6, comprising:
(D) trialkylamine.

8. The ink composition according to claim 6, comprising:
(E) a colorant.

\* \* \* \* \*